(12) United States Patent  
Kimmerling et al.

(10) Patent No.: US 11,530,974 B1  
(45) Date of Patent: Dec. 20, 2022

(54) CELLULAR MEASUREMENT, CALIBRATION, AND CLASSIFICATION

(71) Applicant: Travera, Inc., Medford, MA (US)

(72) Inventors: Robert Kimmerling, Cambridge, MA (US); Selim Olcum, Cambridge, MA (US); Mark Stevens, Cambridge, MA (US)

(73) Assignee: Travera, Inc., Medford, MA (US)

( * ) Notice: Subject to any disclaimer, the term of this patent is extended or adjusted under 35 U.S.C. 154(b) by 0 days.

(21) Appl. No.: 17/729,651

(22) Filed: Apr. 26, 2022

Related U.S. Application Data

(60) Provisional application No. 63/274,255, filed on Nov. 1, 2021.

(51) Int. Cl.
| | | |
|---|---|---|
| *G01N 15/10* | (2006.01) | |
| *G01N 33/50* | (2006.01) | |
| *G01N 9/00* | (2006.01) | |

(52) U.S. Cl.
CPC ............ *G01N 15/10* (2013.01); *G01N 9/002* (2013.01); *G01N 33/5005* (2013.01); *G01N 2015/1043* (2013.01); *G01N 2015/1075* (2013.01)

(58) Field of Classification Search
CPC ... G01N 2015/1043; G01N 2015/1075; G01N 15/1475
See application file for complete search history.

(56) References Cited

U.S. PATENT DOCUMENTS

| | | | |
|---|---|---|---|
| 8,418,535 B2 | 4/2013 | Manalis et al. | |
| 8,639,043 B2 | 1/2014 | Levenson et al. | |
| 9,132,294 B2 | 9/2015 | Zheng et al. | |
| 2010/0288043 A1* | 11/2010 | Manalis | G01N 15/00 73/32 R |
| 2010/0297747 A1* | 11/2010 | Manalis | G01N 15/1056 435/287.3 |
| 2014/0345369 A1* | 11/2014 | Babcock | G01N 11/10 73/54.13 |
| 2016/0174902 A1 | 6/2016 | Georgescu et al. | |
| 2017/0053398 A1 | 2/2017 | Mahoor et al. | |
| 2019/0344278 A1* | 11/2019 | Agache | C12M 33/00 |
| 2022/0011296 A1* | 1/2022 | Ligon | G01N 33/5017 |

FOREIGN PATENT DOCUMENTS

WO 2016/182551 A1 11/2016

OTHER PUBLICATIONS

Ben-Hur, 2001, Support Vector Clustering, J Mach Learning Res 2:125-137.
Breiman, 2001, Random Forests, Machine Learning 45:5-32.
Burg, 2007, Weighing of biomolecules, single cells and single nanoparticles in fluid, Nature 446:1066-1069.
Cermak, 2016, High-throughput measurement of single-cell growth rates using serial microfluidic mass sensor arrays, Nat Biotechnol 34(10):1052-1059.

(Continued)

*Primary Examiner* — Paul M. West
(74) *Attorney, Agent, or Firm* — Brown Rudnick LLP; Thomas C. Meyers

(57) ABSTRACT

The invention provides devices and methods for linked multimodal measurements of individual particles using a mass sensor and an additional sensor.

25 Claims, 8 Drawing Sheets

(56) References Cited

OTHER PUBLICATIONS

Chen, 2016, XGBoost: A Scalable Tree Boosting Measurement device, arXiv:1603.02754 (13 pages).

Criminisi, 2012, Decision Forests: A unified framework for classification, regression, density estimation, manifold learning and semi-supervised learning, Foundations and Trends in Computer Graphics and Vision 7(2-3):81-227.

Freund, 1997, A decision-theoretic generalization of on-line learning and an application to boosting, J Comp Sys Sci 55:119.

Gomes, 2017, A survey of ensemble learning for data stream classification, ACM Computing Surveys 50(2):article23, (36 pages).

Greenbaum, 2012, Imaging without lenses: achievements and remaining challenges of wide-filed on-chip microscopy, Nat Methods 9(9):889-895.

Haridas, 2019, Convolutional Neural Networks: A Comprehensive Survey, International Journal of Applied Engineering Research 14(3):780-789.

Jordan, 2015, Machine learning, Trends, perspectives, and prospects, Science 349(6245):255-260.

Krizhevsky, 2012, ImageNet Classification with deep convolutional neural networks, Chapter in Advances in Neural Information Processing Systems 25, Pereira et al., Eds, NeurIPS Proceedings (9 pages).

Lee, 2011, Suspended microchannel resonators with piezoresistive sensors, Lab Chip 11:645-651.

Simonyan, 2014, Very deep convolutional networks for large-scale image recognition, CoRR, abs/3409.1556 (14 pages).

Szegedy, 2015, Going deeper with convolutions, Computer Science CVPR, arXiv:1409.4842 (12 pages).

Villaverde, 2019, On the adaptability of ensemble methods for distribution classification measurement devices: A comparative analysis, International Journal of Distributed Sensor Networks 15(7) (19 pages).

Wang, 2015, Face Search at Scale: 80 Million Gallery, MSU Technical Report MSU-CSE-15-11, arXiv:1507.07242 (14 pages).

\* cited by examiner

CELLULAR MEASUREMENT, CALIBRATION, AND CLASSIFICATION

TECHNICAL FIELD

The invention relates to methods of for multimodal measurements of individual cells.

BACKGROUND

Cancer is a global health issue that causes millions of deaths annually worldwide. While a cure is the ultimate goal, a more practical near-term goal is to focus on disease management. Other positive outcomes include complete or partial remission in which the cancer has responded to a treatment and is either significantly reduced (partial remission) or undetectable via radiological imaging or histological examination (complete remission).

Unfortunately, remission is often temporary, and cancer often recurs or progresses after initially responding to treatment and maintenance therapies. Cancer cells can change through continued mutation and cancers can often develop resistance to previously-effective therapies. While there is some effort to tailor treatment, there is limited ability to effectively predict how an individual patient will respond to a particular treatment. Moreover, traditional methods for measuring cancer biomarkers after treatment do not provide the requisite precision necessary to drive therapeutic choice, which may lead to extended periods of time in which a patient endures a treatment that simply isn't working as intended.

Cellular mass and density and changes in cellular mass and density have emerged as critical biomarkers of cell disease and response to treatment. Suspended microchannel resonators (SMR) are an ideal means by which to obtain these cellular measures at a single cell resolution. However, due to the configuration and operation of SMRs, there have not been measurement devices and methods that provide multimodal measurements, which combine single cell measurements performed by SMR sensors with other sensor types and measurement modalities of single cells.

SUMMARY

The present invention provides methods and measurement devices for precisely measuring particles using a suspended microchannel resonator (SMR) in combination with other measurements to provide multimodal measurements. Measurement devices of the invention comprise a measurement device having a channel through which a stream of particles flows through a sensor to measure particle mass and at least one additional sensor to measure a property independent of mass. Preferably measurements from each sensor are linked for each particle.

In a preferred embodiment, the particles are cells and measurement devices and methods of the invention identify the cells and determine their flow velocity and/or trajectory through the SMR and/or by any other means utilized for multi-modal measurement. In prior measurement devices and methods, it was not possible to track cells or to perform simultaneous, linked multimodal measurements as cells flowed through an SMR. By identifying a cell with a first type of sensor and determining the velocity and/or trajectory of its flow through a microchannel, the presently disclosed measurement devices and methods are able to track an individual cell (or populations of cells) as it passes by (e.g., the SMR and an optical sensor) and correlate measurements from those sensors with respect to a cell or cells. Any particle or group of particles can be used in practice of the invention and include, but are not limited to, tissue debris, cell aggregates, bacteria, fungi, protein, protein aggregates, exosomes, and biologically functionalized particles.

In methods and measurement devices of the invention, particles are introduced into a measurement device that includes one or more microchannels through which the particles flow. A sensor, such as a brightfield imager placed in series with the SMR, provides data to a classifier that identifies a particle that has flowed, or will flow, through an SMR. The measurement device determines the velocity and/or trajectory of the particle flowing through the microchannel. Using the flow velocity and/or trajectory, the measurement device correlates measurements made using the SMR and the additional sensor(s). As used herein, reference will be made to a preferred embodiment in which cells are the particles, but it is understood that any particles may be used in the context of the invention as determined by the user.

In certain aspects, measurement devices described herein use the SMR to determine the flow velocity of a cell passing through it. A single-cell mass measurement collected with the SMR is derived from the magnitude of frequency shift peaks caused by the cell traversing the sensor. However, the temporal characteristics of that peak may also be used to determine the velocity as well as flow path of the cell traversing the sensor. The measurement device may use this flow velocity and/or flow path to project a time when a cell passed through a sensor region, either upstream or downstream of the SMR. The measurement device uses this projected time to correlate the SMR measurement with the identity of a cell, which was obtained by the classifier using data from a sensor (e.g., a brightfield imager) as the cell passed through the sensor region. Thus, the velocity provides a time shift that may be used to find the corresponding measurement (e.g., image of a particular cell) associated with a given mass measurement from the SMR.

Similarly, in certain aspects, measurement devices provided herein may use correlation statistics to identify and match measurements performed by multiple sensors (including the SMR) serially connected in the measurement channel, without first calculating the flow velocity of a cell. By using correlation between the time series of measurements performed at each sensor, the measurements are linked with high accuracy. In such measurement devices, the magnitude of the measured signals in each sensor can be additionally utilized to improve the accuracy of the process of matching measurements of different sensors. One example is to use the size calculated from a brightfield image to correlate with the mass measured by the SMR in addition to using the time of measurements of image capture and SMR measurement.

Similarly, in certain aspects, measurement devices of the invention may use the sensor(s) in a sensor region to provide data to a classifier that identifies a single cell and its characteristics and determines its flow velocity. For example, certain measurement devices and methods of the invention use an imaging sensor, such as a brightfield sensor, to provide data to a classifier. The classifier uses those data to identify a cell that will or has passed through an SMR. The sensor may obtain multiple measurements, such as images with a brightfield sensor, to track the position of the identified cell at multiple time points to calculate its flow velocity. Using the flow velocity, the measurement device projects a time at which the identified cell passed through the SMR. The measurement device correlates an SMR measurement obtained near the projected time with the identity of the cell. The time difference measured from multiple sensor measurements, e.g., images, collected in succession for the same cell are used to determine the cell velocity, which may be used to project the time of a cell's mass measurement for data matching. Independent measurements by the sensors are linked by correlating a time difference between measurements of single particles across the mass sensors and other sensors. These signals (and correlations based on them) can be made in real time. In a preferred feature of the invention, linked measurements from the sensors are used to classify particles into groups based on orthogonal information acquired from the linked measurements. The invention is useful to categorize or group cells generally and may be applied to identify cellular vs. non-cellular material and/or living vs. dead cells. Sensors can be controlled by any means necessary. However, in a preferred embodiment, one of the sensors is an SMR and the sensors are controlled by a field programmable gate array (FPGA).

In certain aspects, multimodal measurements obtained using the measurement devices and methods of the invention are used to reciprocally improve the quality or interpretability of each data set (one from the SMR and the other from the sensor in the sensing region) in isolation. For example, brightfield imaging conducted upstream of an SMR is useful to determine when multiple cells are entering the SMR concurrently. Certain measurement devices and methods of the invention use that information from the imager to deconvolve the coupled mass peak obtained from the SMR. Without that information, this type of multi-peak mass measurement from an SMR would be uninterpretable and need to be discarded. Similarly, imaging may be used to determine the flow path of a cell entering the SMR. Certain measurement devices and methods of the invention correct SMR measurements for position-dependent error in certain types of SMR-based mass readouts (e.g., first mode mass sensing, second mode short channel sensing). Single-cell mass measurements may also be used to improve the classification of single-cell image sets (e.g., specifying a mass threshold or mass based "cost" of image classification for live versus dead, or tumor versus immune cells).

Thus, the present invention provides methods and measurement devices for assessing cellular properties. An exemplary measurement device of the invention includes a measurement device with a measurement channel through which a cell flows, a sensor operating over a sensing region in the channel, and a suspended microchannel resonator (SMR). In certain aspects, the measurement device identifies a cell flowing through the measurement channel utilizing data from the sensor, determines a flow velocity of the cell, and correlates a measurement obtained using the SMR with the identity of the cell.

In certain aspects, the measurement device provides multi-modal measurements for a single cell that include one or more of the cell's mass, volume, diameter, impedance, capacitance, optical properties, fluorescence intensity, density, stiffness, surface friction, and deformation. In such measurement devices, the linked multi-modal measurements may be used independently to provide an additional dimension to the single-cell data, e.g., using a cell's mass and optical properties, such as fluorescence signal from specific surface markers. In other measurement devices, the linked multi-modal measurements may be used to calculate a dependent, yet otherwise inaccessible parameter of the cell, e.g., using linked mass and volume measurements of a single cell to calculate cell's density, or using linked mass and deformation measurement of a single cell to calculate cell's stiffness. In other measurement devices, the linked multi-modal measurements are used to calculate a parameter that is correlated to a physical property of the cell, e.g., using linked mass and optical diameter to calculate a parameter that is proportional to cell's volume and density.

A cell can flow through the sensor region prior to or after the SMR. The measurement device may use the flow velocity of the cell to project a time at which the cell flows through the SMR for measurement. The measurement device uses this projected time to correlate a measurement obtained using the SMR with the identity of a cell.

In certain aspects, the sensor at the sensing region is an imaging sensor. In certain aspects, the measurement device identifies the cell using an image obtained with the imaging sensor prior to or when the cell enters the SMR for measurement. The imaging sensor may obtain a plurality of images of the cell as it flows over the sensing region and the measurement device determines the flow velocity of the cell using a positional change of the cell between each of the images. In certain measurement devices, the imaging sensor images across multiple imaging fields. The multiple imaging fields may include multiple sensing regions associated with an SMR and/or serial SMRs.

In certain aspects, the measurement device incorporates a fluorescence sensor at the sensing region, e.g., a fluorescence optics connected to a photomultiplier tube sensor to detect the presence and/or measure the magnitude of a fluorescence signal from the cell. In such measurement devices, the fluorescence signal may be used to identify the cell of origin, cell type, cell state, cell viability, activation state, differentiation state, and used together with cell's mass.

Certain measurement devices of the invention include a plurality of SMRs and/or sensor regions. In certain aspects, each sensor region is associated with a different SMR, and the sensor(s) (e.g., an imaging measurement device) measures cells flowing in each sensor region. For example, an imaging sensor may image multiple sensor regions using a different field of view for each sensor region.

In certain aspects, the measurement device uses data from the SMR to determine the flow velocity of the cell. The measurement device may project a time at which a cell flowed through the sensor region using the flow velocity. The measurement device may correlate a measurement obtained using the SMR with the identity of the cell using the projected time. In certain measurement devices, the measurement device determines flow velocity of the cell using a width of frequency shift peaks measured by the SMR as the cell flows through the SMR. In certain embodiments, the measurement device determines the velocity of the cell using the temporal variation of the frequency shift signal measured by the SMR as the cell flows through the SMR.

In certain measurement devices, the velocity of the cell is determined using the frequency shift signals from multiple vibrational modes of the SMR. Use of multiple vibrational modes of the SMR provides an accurate measurement of the flow path and thus reduces the variability on the flow velocity estimate.

In certain aspects, the sensor detects the orientation of the cell in the measurement channel. The measurement device may use this orientation data to adjust a measurement of the cell obtained using the SMR due to the detected orientation of the cell. In certain aspects, the sensor detects the cell entering the SMR with one or more other cells. The measurement device uses data from the sensor to isolate a mass measurement for each of the cells from a convoluted frequency shift measurement obtained by the SMR, due to the cell and the one or more other cells flowing through the SMR.

In other measurement devices of the invention, the SMR is connected to at least one measurement channel that is larger in cross-section compared to the cross section of the channel running through the SMR. A wide cross-section channel in the sensor region reduces the flow velocity of cells enabling higher quality measurements (e.g., imaging, fluorescence, impedance, capacitance), while a narrow channel cross section in SMR increases SMR sensitivity for measuring cell mass and decreases position dependent error on velocity estimates.

In some measurement devices of the invention, the SMR is placed in the middle of two measurement channels, enabling linked multi-modal measurements at multiple sensor regions before and after the cell is measured in the SMR.

In another embodiment of the invention, an array of SMRs is placed in series with an array of measurement channels. In such measurement devices, the SMRs and sensors (e.g., fluorescence, impedance, capacitance) are operated simultaneously but independently. In other measurement devices, a single sensor (e.g., brightfield imaging) can be placed to capture all measurement regions of the array.

In certain measurement devices, both the SMR and the sensor signals are measured and processed by a FPGA to provide real-time linked measurements of a cell flowing in the measurement channel.

In certain measurement devices, the measurement channel is placed in between a sample channel and a waste channel, to control flow into and out of the measurement channel. In such measurement devices, an additional sensor can be placed at the entrance and exit regions to identify flow conditions in the sample and waste channels.

measurement devices of the invention are useful to identify one or more biological property of the cell using a combination of data from the sensor and the SMR.

In certain aspects, the measurement device determines whether the cell or any other debris in the sample stops flowing through the measurement channel due to a blockage.

DETAILED DESCRIPTION

The present disclosure provides methods and measurement devices for optimized multimodal measurements of individual cells using a suspended microchannel resonator (SMR) and one or more other sensors in order to effectively detect biomarkers and other properties of cells. The presently disclosed measurement devices and methods combine the high-resolution capabilities of an SMR to obtain accurate measurements, such as mass-, density-, and velocity-based measurements of single cells with other forms of measurement, such as optical measurements, to provide high throughput means of obtaining multimodal measurements for individual, living cells.

Measurement devices and methods of the invention identify single cells flowing through a microchannel of a measurement device. Measurement devices of the invention identify an individual cell using a sensor as the cell flows past a sensor region in a microchannel before and/or after the cell passes through an SMR for measurement. The measurement device may provide data from the sensor to a classifier that identifies and tracks the cell through the measurement device. Measurement devices and methods of the invention include a step that determines the flow velocity of an identified cell through a microchannel of the measurement device. Using the flow velocity, the measurement device correlates a measurement/identity of the cell from a sensor, such as a brightfield imager, with a measurement obtained for that same cell using the SMR.

Measurement devices of the invention may also track individual cells as they flow past a series of sensor regions and/or SMRs. In this way, measurement devices and methods of the invention provide multimodal measurements of a single cell over time, which may include SMR derived measurements, such as cellular mass and density.

Figure 1:
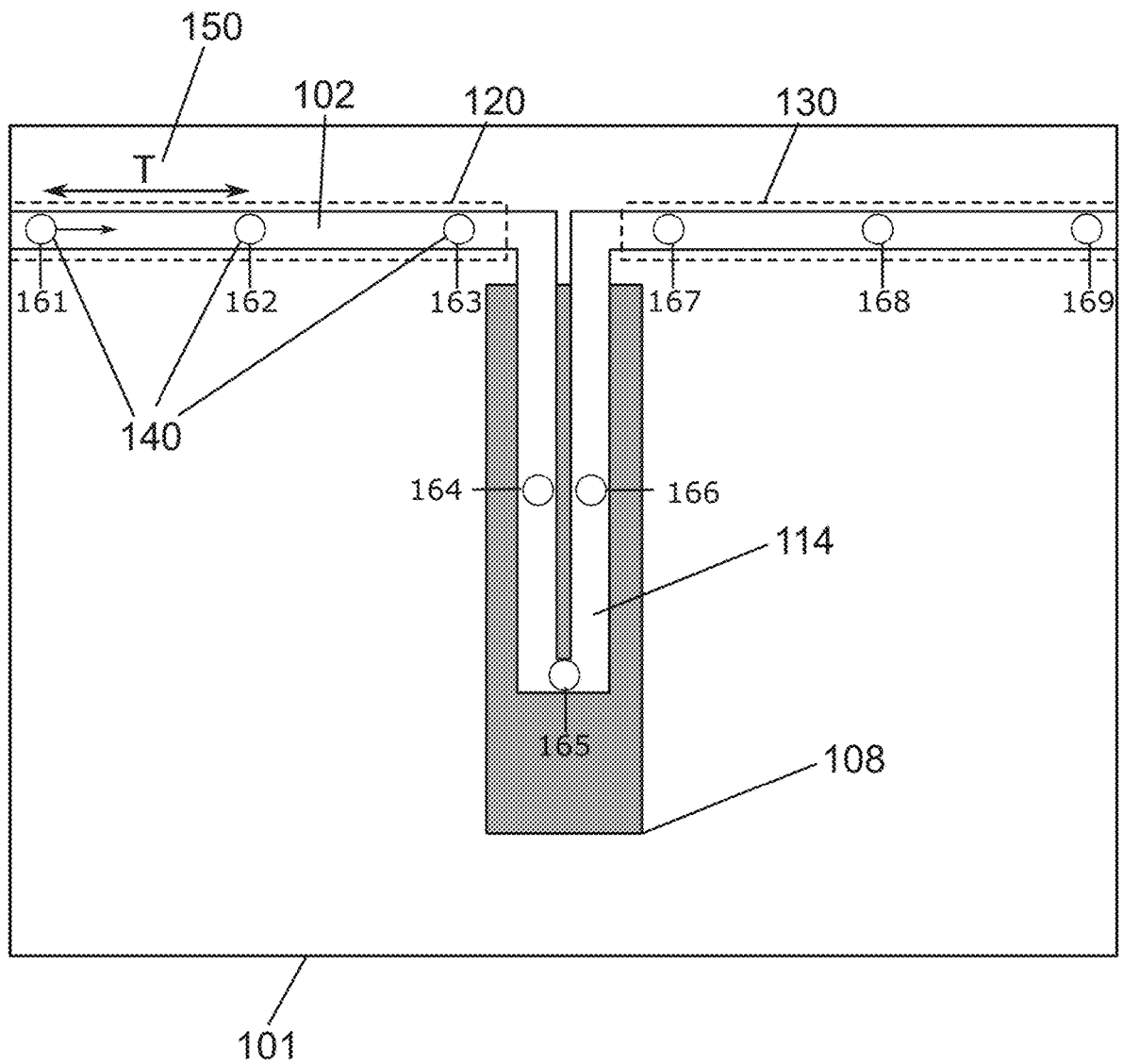
FIG. 1 diagrams an exemplary SMR used in the invention.

FIG. 1 diagrams an exemplary SMR device that is used as the mass sensor in the methods and measurement devices of the invention to provide a multimodal measurement for single cells. The device includes a measurement channel 102 through which cells flow. An SMR sensor 108, which includes an integrated fluidic channel 114 running through it, is placed along the measurement channel. The device also includes one or more sensing regions 120, 130, over which at least one additional sensor, which is not the SMR, operates to obtain one or more measurements of a single cell. For example, in exemplary measurement devices of the invention, this additional sensor is an imaging sensor, such as a brightfield sensor, which obtains one or more images of the single cell.

In certain measurement devices of the invention, the channel integrated in the SMR 114 has a smaller cross-section than the measurement channel at either side of the SMR, on which the sensor region(s) is located. A bigger cross-section channel in the sensor region proportionally reduces the flow velocity of cells enabling higher quality measurements (e.g., imaging), while a smaller channel cross-section in the SMR increases sensor sensitivity and decreases position dependent error. Similarly, the fluidic channel within the sensor regions 120 and 130 may be further configured to focus the flow of cells relative to the X, Y, and Z dimensions to prevent cells from stacking or passing one another in the microchannels of device. This may help assure that a determined flow velocity remains associated with a particular cell.

In certain aspects, the additional sensor provides data or a signal as a cell passes through the sensing region that the measurement device uses to classify an individual cell vs cellular debris, cell aggregates or to identify if a cell is alive or dead. As shown, the sensing regions may be positioned across the measurement channel before 120 and/or after 130 the SMR. In certain aspects, the additional sensor uses measurements from the sensing regions to determine the flow velocity of an identified cell. For example, as shown in FIG. 1, the measurement device may obtain measurements of a single cell at multiple time points 140, while the cell is in a sensing region 120 and/or 130. The time difference 150 it takes for a cell between measurements of the additional sensor is used to calculate the flow velocity of an individual cell in the measurement channel 102. In certain aspects, the sensor is an imaging sensor that obtains multiple images of a single cell as it flows through the sample channel.

The measurement device may use the flow velocity data to project a time when a cell flows or flowed past the SMR. Using this projection, the measurement device correlates a mass measurement made by the SMR at or near the projected time with the independent measurement(s) made by the additional sensor(s). Thus, the measurement device is able to track the path of an individual cell through an SMR and one or more additional sensors to provide a multimodal assessment of the cell. In certain aspects, the mass of a cell measured by the SMR is linked with the identification of a cell such as live vs dead or classification of a cell such as single cell, aggregate or tissue debris.

In some embodiments, one of the additional sensors in the measurement device is a fluorescent detector and the mass of a cell measured by the SMR is linked with a fluorescent marker of the cell reporting a cell property such as cell origin, cell viability, cell type, cell-cycle state, cell differentiation state, activation state, etc.

Optionally, one of the additional sensors in the measurement device measures an additional independent physical or mechanical property and the mass of a cell measured by the SMR is linked with its density, volume, dry density, deformability, elasticity or stiffness.

Figure 2:
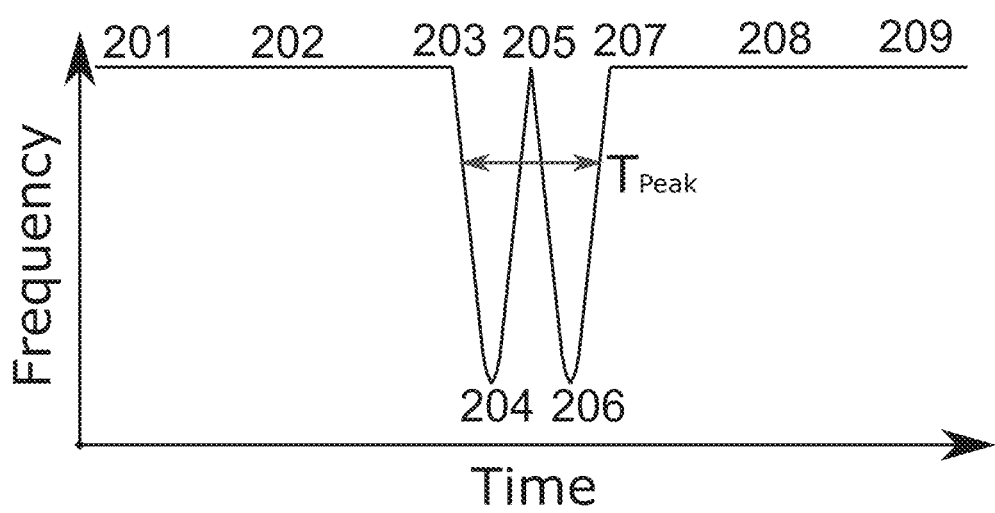
FIG. 2 shows exemplary SMR waveform with corresponding cell positions

Measurement devices of the invention may use the transient signal created by the SMR to determine the flow velocity of a cell in the measurement channel. FIG. 2 provides an exemplary measurement of a single-cell mass collected using an SMR. The signal locations 201-209 correspond to physical locations 161-169 on measurement channel 102. The magnitude of frequency shift peaks in FIG. 2 are caused by the cell traversing the measurement channel 120 and the channel embedded in the SMR 114, and may provide, for example, mass- and density-based measures of the cell. However, the time dynamics of this peak such as its full width, full width at half maximum or the shape may also be used to determine the velocity of the cell traversing the SMR. The measurement device may use this flow velocity to project a time when a cell passed or will pass through a sensing region(s), upstream 120 and/or downstream 130 of the SMR. The measurement device uses this projected time to correlate the SMR measurement with the identity of a cell determined using data from an additional sensor (e.g., an imager) operating over the sensor region(s). Thus, the velocity provides a time difference that may be used to find the corresponding measurement (e.g., image of a particular cell) associated with a given mass measurement from the SMR.

In certain aspects, data from the additional sensor operating over the sensor region is sent to a classifier trained to identify single cells. When a cell flows into the sensing region, which comprises a sensor operating over the sensing region, data from the sensor may be provided to a classifier which identifies the cell. In certain aspects, the classifier uses data from the sensor to identify cellular, non-cellular material, target cells, non-target cells, labels, and/or clogs in the device. In certain aspects, the classifier determines the flow velocity and correlates measurements from the SMR with those obtained for a single cell using a sensor operating over the sensor region.

Figure 3:
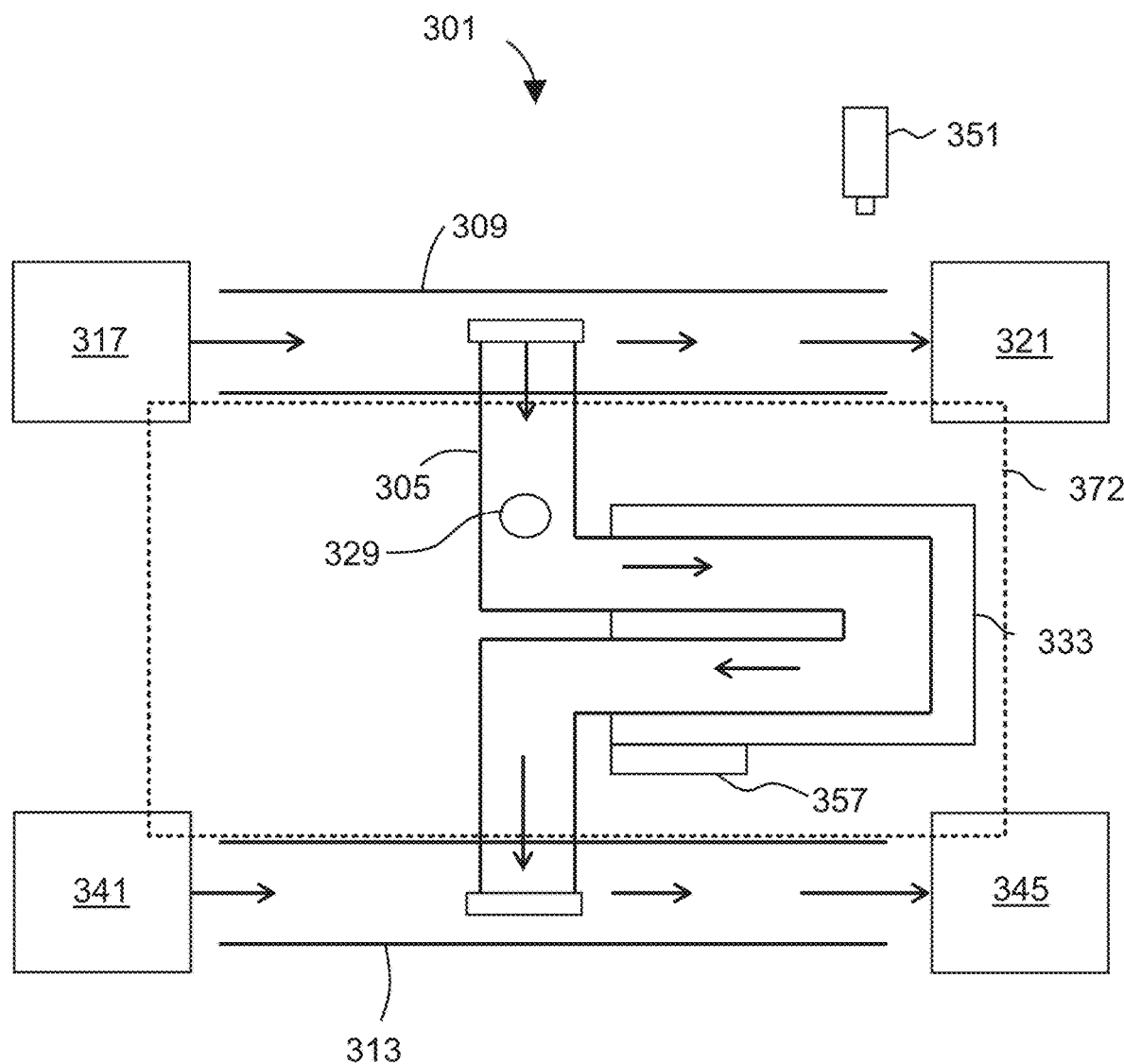
FIG. 3 shows a suspended microchannel resonator (SMR) device optimized for multimodal measurements.
Figure 3:
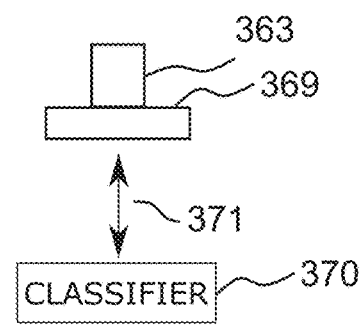

FIG. 3 shows a suspended microchannel resonator (SMR) device 301 of the disclosure. The measurement device 301 includes a sample channel 309 and a secondary channel 305. Cells are introduced into the sample channel and flow through the sample channel 309 to a sensing region anywhere along the channel accessible by a sensor 363. The sensor 363 may operate over the sensing region and collect data from an individual cell as if flows through the sensing region. The measurement device uses data from the sensor 363 to identify the single cell. This may include providing the data 371 to a classifier 370. The classifier may use the data from the sensor 363 to identify and track individual cells flowing through sensing region. The measurement device determines the velocity at which the cell 329 flows, for example, as it enters the measurement channel 305 for measurement by the SMR 333. The flow rate through the SMR device can be controlled based on the identification of individual cells in the SMR device, using data 371 from sensors 363 disposed over one or more sensor regions. This data may be provided to a classifier 370, which is trained to identify and track individual cells.

In certain respects, the classifier identifies cellular and/or non-cellular material in the sample channel 309. The measurement device may comprise a control measurement device for receiving the identification from the classifier 370 and control and track the flow of individual cells through the sample channel 309 and the measurement channel 305. The measurement includes a suspended microchannel resonator (SMR) 333, for making optimized single cellular measurements, such as mass-, density, and velocity-based measurements.

Cells in an eluate 317 flow through the upper sample channel 309, wherein a portion of the eluate 317 collects in the upper sample channel waste reservoir 321. The calibration method is being depicted. A cell 329 is introduced into the channel 305. A portion of the eluate 317 including the cell 329 flows through the suspended microchannel 333. The particle has previously been identified by a classifier, and the flow velocity through the suspended microchannel 305 has been determined. The velocity may be controlled by adjusting the pressure difference between the inlet and outlet of the channel to optimize measurement of the particle of non-cellular material. Velocity may also be controlled by providing channels of varying diameter.

In the exemplary device of FIG. 3, since the flow cross section of the suspended microchannel 333 and measurement channel 305 is about 70 times smaller than that of the sample channel 305, the linear flow rate can be much faster in the suspended microchannel than in the sample channel, even though the pressure difference across the suspended microchannel is small. Therefore, at any given time, it is assumed that the SMR device 301 is measuring the eluate that is present at the inlet of the suspended microchannel. This helps assure the projected time at which the cell flows past the sensor or SMR can be accurately determined, as there is a constant measurement point.

The cell 329 flows through the suspended microchannel 305. The suspended microchannel 305 extends through a cantilever 333 which sits between a light source 351 and a photodetector 363 connected to a chip 369 such as a field programmable gate array (FPGA). The cantilever 333 is operated on by an actuator, or resonator 357. The resonator 357 may be a piezo-ceramic actuator seated underneath the cantilever 333 for actuation. After the cell 329 is introduced to the lower waste channel 313, the cell 329 is collected in the lower waste collection reservoir 345. A cell 329 identified by the classifier flows from the upper sample channel 309 to the inlet of the measurement channel 305, through the suspended microchannel 333, and to the outlet of the suspended microchannel toward the lower waste channel 313. A buffer 341 flows through the lower bypass channel towards a lower bypass channel collection reservoir 345.

By flowing the cell 329 through the SMR device 301 a reading or measurement may be made. This measurement is correlated with the identity of the cell to provide a multi-modal measurement. The dotted region 372 captures the area depicted in FIG. 1. In certain aspects, the readout of the measurement from the SMR may be adjusted based on information provided by the sensor disposed over the sensor region and/or the classifier. For example, the sensor may detect the orientation of the cell in the sample channel, e.g., by using an image or set of images obtained from the sensor. The measurement device or classifier may use this orientation data to adjust a measurement of the cell obtained using the SMR, which would otherwise be inaccurate due to the detected orientation of the cell. Similarly, the sensor may detect the cell entering the SMR with one or more other cells. A measurement made using the SMR as a number of cells pass through it together can result in multi-peak measurements. The measurement device or classifier may use data from the sensor indicative of multiple cells traversing the SMR to isolate a measurement for a particular cell from a multi-peak measurement obtained by the SMR.

In certain measurement devices of the invention, the SMR is suspended within the sample channel and a diameter of a portion of the channel in which the SMR is suspended is narrower than a diameter of a portion of the channel in which the sensor region is located. A wide diameter channel in the sensor region reduces the flow velocity of cells for higher quality measurements (e.g., imaging), while a narrow channel diameter in SMR to increases sensor sensitivity and decreases position dependent error.

In certain aspects, the classifier identifies one or more biological property of the cell using a combination of data from the sensor and the SMR.

In certain aspects, the classifier determines whether the cell stops flowing through the sample channel due to a blockage.

The SMR device 301 when used with the measurement devices and methods of the disclosure provides real-time, high-throughput optimized monitoring of mass or density of individual cells flowing therethrough and correlates those measurements with the identity of a single cell. Therefore, the cellular measurements, including mass and/or mass changes (e.g., MAR), of a single cell can be precisely measured. Such data can be stored and used in subsequent analysis steps.

The measurement device may comprise an SMR device 301 comprising an array of SMRs with a fluidic channel passing 305 therethrough. For example, the measurement device may comprise a serial SMR (sSMR) in which fluid passes through an array of SMR devices, in which each successive pair of SMR devices is separated by a portion of the channel that provides a delay. The flow of fluid in each SMR may be controlled based on a classifier 255 that identifies and tracks individual cells flowing through the sSMR. The sSMR may include multiple SMRs and sensor regions that are fluidically connected, such as in series, and separated by delay channels for optimized cellular measurements.

Devices used in certain methods and measurement devices of the invention may comprise a suspended microchannel resonator (SMR) 301 or serial SMR (sSMR) for precisely making cellular measurements, such as density and mass and/or changes in density or mass, of materials flowing through the device. The SMR device 301 comprises an exquisitely sensitive scale that detects minor weight or density changes in cells. The SMR device 301 includes a structure such as a cantilever that contains a fluidic microchannel. Individual cells are flowed through the structure, which is resonated, and its frequency of resonation is measured. The frequency at which a structure resonates is dependent on its mass. By measuring the frequency at which the cantilever resonates when cell is at a first point along the cantilever, the instrument may compute a mass/density, or change in mass/density of the particle in the fluidic microchannel.

By measuring the deviation of the resonant frequency at which the cantilever resonates when a cell is at a second point along the cantilever, the instrument may compute structural properties of the particle in the fluidic microchannel, and the data may be used by a classifier to identify additional properties of an identified cell. In one aspect, the measurement device determines flow velocity of the cell using a width of frequency shift peaks measured by the SMR as the cell flows through the SMR.

By flowing particles cellular and/or non-cellular material through such devices, properties of the particles can be observed. For example, by flowing cells through such devices, it can be determined whether or not identified cells are growing and accumulating mass and/or density. By flowing non-cellular material through such devices, for example reference material with a known property, measurements and devices can be calibrated. The mass or density accumulation or rate of mass or density accumulation is a clinically important property and is used to indicate cellular identity and/or activity. The speed and sensitivity of an SMR device 301 allows the SMR device 301 to detect, for example, a cell's response to a treatment modality while the cell is still living. Suspended microchannel resonator devices 301 are described in Cermak, 2016, High-throughput measurement of single-cell growth rates using serial microfluidic mass sensor arrays, Nat Biotechnol, 34(10): 1052-1059, incorporated herein by reference.

Figure 4:
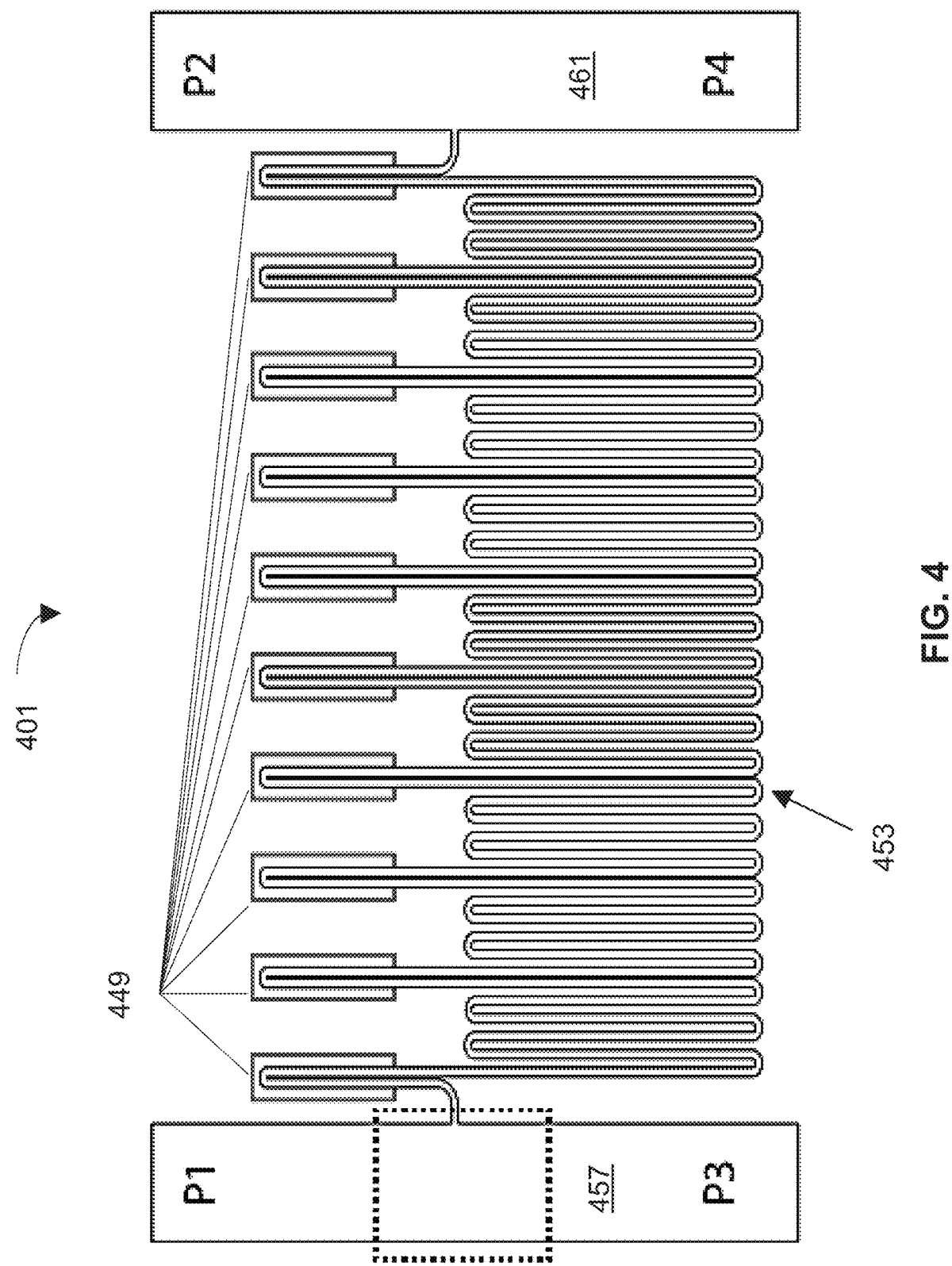
FIG. 4 shows a serial suspended microchannel resonator (sSMR) array.

FIG. 4 shows a serial suspended microchannel resonator (sSMR) array 401. Instruments may include one or more sSMR array 401 to make reliably sensitive and precise measurements of mass and density or changes in mass and density. Each individual SMR may include a sensing region over which a sensor operates to obtain measurements, which may be used to track a cell or measure its flow velocity.

Instead of a single suspended microchannel device 301, the instrument may include an sSMR array 401, which includes a plurality of cantilevers 449 and a plurality of delay channels 453. A live cell may be identified by a classifier and then introduced into a first bypass channel 457 through the cantilevers 449 and delay channels 453 to the second bypass channel 461. Pressure differences in the first bypass channel 457 are indicated by P1 and P2, and pressure differences in the second bypass channel 461 are indicated by P3 and P4. The pressure differences in the first and second bypass channels may be controlled based on the identification of the cell in the sSMR using one or more sensors operating on one or more sensing regions of the device.

The live cell flows through the sSMR array 401, which is resonated and its frequency of resonation is measured. In each cantilever in the array of cantilevers 449 the frequency at which a structure resonates when the cell is at a first point along the cantilever is dependent on its mass and by measuring the frequency at which the cantilever resonates, the instrument may compute, for example, a mass, change in mass, density, change in density, and/or velocity of a living cell using the SMR. By flowing a live malignant cell through such devices, one may observe functions of those cells, such as whether they are growing and accumulating mass/density or not. The mass or density accumulation or rate of mass or density accumulation may be related to clinically important property such as the presence of a cancer cell or the efficacy of a therapeutic on a cell. In each cantilever in the array of cantilevers 449 the deviation of the resonant frequency at which the structure resonates when the cell is at a second point along the cantilever is dependent on structural properties of the cell and can be used to identify the cell as cellular material.

Various embodiments of SMR devices 301 and sSMR instruments 401, as well as methods of use, include those instruments/devices manufactured by Innovative Micro Technology (Santa Barbara, Calif.) and described in U.S. Pat. Nos. 8,418,535 and 9,132,294, all incorporated by reference. Notably, SMR devices 301 and sSMR instruments 401 may be used together with a classifier 255 for optimized cellular measurements.

Cantilevers of an SMR device 301 of sSMR instrument 401 may be housed in an on-chip vacuum cavity, reducing damping and improving frequency (and thus mass) resolution for optimized measurements, which may be correlated with the identity of a particular cell. As a particle cell previously identified, including by a classifier, flows through the interior of the cantilever, it transiently changes the resonant frequency of the cantilever in proportion to the buoyant mass of the particle. SMR devices 301 may weigh single mammalian cells with a resolution of 0.05 pg (0.1% of a cell's buoyant mass) or better. Where mass, MAR, density, and/or density accumulation rate, is measured, devices of the disclosure are provided that are capable of measuring these properties within certain valuable sensitivities or times from the cells identified by a classifier.

For example, mass measurement instruments that use a suspended microchannel resonator (SMR) device 301 are capable of measuring mass, mass change, or MAR with a precision of at least about 0.01% of a cell mass. SMR-based instruments are capable of measuring mass, mass change, density, density change, density accumulation rate, or MAR with a precision of at least about 0.1% per hour.

Embodiments of the technology use microchannel resonators to precisely measure mass, density, mass changes, and/or density changes in individual living cells after identification of the cell the measurement device using data from another sensor. The sSMR array 401 includes an array of SMR devices fluidically connected in series and separated by delay channels between each cantilever 449. The delay channels give the cell time to grow as it flows between cantilevers.

SMR devices 301 to be used together with a classifier may be fabricated as described in Lee, 2011, Suspended microchannel resonators, Lab Chip 11:645 and/or Burg, 2007, Weighing of biomolecules, Nature 446:1066-1069, both incorporated by reference. Large-channel devices (e.g., useful for peripheral blood mononuclear cells (PBMC) measurements) may have cantilever 333 interior channels of 15 by 20 μm in cross-section, and delay channels 20 by 30 μm in cross-section. Small-channel devices (useful for a wide variety of cell types) may have cantilever 333 channels 3 by 5 μm in cross-section, and delay channels 4 by 15 μm in cross-section. The tips of the cantilevers 449 in the sSMR array 401 may be aligned so that a single line-shaped laser beam can be used for optical-lever readout. The cantilevers may be arrayed such that the shortest (and therefore most sensitive) cantilevers are at the ends of the array. Before use for measuring, the sSMR array 401 may be cleaned with piranha (3:1 sulfuric acid to 50% hydrogen peroxide) and the channel walls may be passivated with polyethylene glycol (PEG) grafted onto poly-L-lysine. In some embodiments, a piezo-ceramic actuator seated underneath the device is used for actuation. The SMR device 301 may include low-noise photodetector, Wheatstone bridge-based amplifier (for piezo-resistor readout), and high-current piezo-ceramic driver. To avoid the effects of optical interference between signals from different cantilevers (producing harmonics at the difference frequency), the instrument may include a low-coherence-length light source (675 nm super-luminescent diode, 7 nm full-width half maximum spectral width) as an optical lever. After the custom photodetector converts the optical signal to a voltage signal, that signal is fed into an FPGA board, in which an FPGA implements twelve parallel second-order phase-locked loops which each both demodulate and drive a single cantilever. The FPGA may be a Cyclone IV FPGA on a DE2-115 development board operating on a 100 MHz clock with I/O provided via a high-speed AD/DA card operating 14-bit analog-to-digital and digital-to-analog converters at 100 MHz.

To operate all cantilevers 449 in the sSMR array 401 in order to measure cell identified by the measurement device, the resonator array transfer function is first measured by sweeping the driving frequency and recording the amplitude and phase of the array response. Parameters for each phase-locked loop (PLL) are calculated such that each cantilever-PLL feedback loop has a 50 or 100 Hz FM-signal bandwidth. The phase-delay for each PLL may be adjusted to maximize the cantilever vibration amplitude. The FM-signal transfer function may be measured for each cantilever-PLL feedback loop to confirm sufficient measurement bandwidth (in case of errors in setting the parameters). That transfer function relates the measured cantilever-PLL oscillation frequency to a cantilever's time-dependent intrinsic resonant frequency. Frequency data for each cantilever may be collected at 500 Hz, and may be transmitted from the FPGA to a computer. The device may be placed on a copper heat sink/source connected to a heated water bath, maintained at 37 degrees C.

The sample is loaded into the device from vials pressurized under air or air with 5% CO2 through 0.009 inch inner-diameter fluorinated ethylene propylene (FEP) tubing. The sample may comprise cellular and/or non-cellular material together. The pressurized vials may be seated in a temperature-controlled sample-holder throughout the measurement. FEP tubing allows the device to be flushed with piranha solution for cleaning, as piranha will damage most non-fluorinated plastics. To measure a sample of cells, the sSMR array 401 may initially flushed with filtered media. Particles of cellular and/or non-cellular material may be identified by a classifier and then provided to the sSMR 401. The flow velocity of identified cells through the sSMR 401 may be based on data from the sensors used to provide an identification for the cell.

On large-channel devices, between one and two psi may be applied across the entire array based on the identification of cell by the measurement device, yielding flow rates on the order of 0.5 nL/s (the array's calculated fluidic resistance is approximately 3×10^16 Pa/(m3/s). For small-channel devices, 4-5 psi may be applied across the array, yielding flow rates around 0.1 nL/s based on the identification of the cell by the measurement device. Additionally, every several minutes new sample may be flushed into the input bypass channel to prevent particles and cells from settling in the tubing and device. Between experiments, devices may be cleaned with filtered 10% bleach or piranha solution. In certain aspects, the measurement devices detect a drop in velocity of one or more cells through the device to determine that a blockage exists.

For the data analysis, the recorded frequency signals from each cantilever 449 may be rescaled by applying a rough correction for the different sensitivities of the cantilevers. For example, particles of non-cellular reference material identified by the measurement device may be used to calibrate the cantilevers of the device. Cantilevers differing in only their lengths should have mass sensitivities proportional to their resonant frequencies to the power three-halves. Therefore, each frequency signal is divided by its carrier frequency to the power three-halves such that the signals are of similar magnitude. To detect peaks, the data are filtered with a low pass filter, followed by a nonlinear high pass filter (subtracting the results of a moving quantile filter from the data). Peak locations are found as local minima that occur below a user-defined threshold. After finding the peak locations, the peak heights may be estimated by fitting the surrounding baseline signal (to account for a possible slope in the baseline that was not rejected by the high pass filter), fitting the region surrounding the local minima with a fourth-order polynomial, and finding the maximum difference between the predicted baseline and the local minima polynomial fit. Identifying the peaks corresponding to non-cellular reference materials identified by the classifier allows one to estimate the mass sensitivity for each cantilever, such that the modal mass for the particles is equal to the expected modal mass. Peaks at different cantilevers 449 that originate from the same cell are matched up to extract single-cell growth information.

Precision frequency detection following identification of cells by a measurement device of the invention allows the SMR device 301 to measure resonant frequency and mass or density of single living cells. Precision is the closeness of agreement between independent test results. When determining SMR resonance frequency optically, the use of an external laser and photodiode are required and cannot be easily arrayed for multiplexed measurements. Electronic detection of SMR resonance frequency may be attained by fabricating piezo-resistive sensors using ion implantation into single crystal silicon resonators. The mass resolution achieved with piezo-resistive detection, such as 3.4 femtogram (fg) in a 1 kHz bandwidth, is comparable to what can be achieved by a conventional optical detector designed to weigh micron-sized particles and cells.

The use of an SMR device 301 together with the classifier 255 provides the advantage of eliminating the need for expensive, delicate optical components and provides new uses for the SMR device 301 in multiplexed and field deployable applications. For example, piezo-resistive sensors eliminate the need for external components by measuring deflection through the resistance change of a sensing element integrated onto the cantilever. Microfluidic channels are incorporated inside a cantilever resonator, which significantly reduces viscous damping from fluid and allows buoyant mass to be measured with high resolution. Use of a classifier to identify particles before being introduced to the SMR device 301 allows for flow through microfluidic channels to be controlled to optimize measurements.

Methods for optimized cellular measurement may comprise introducing cells into a measurement device comprising a sample channel, a secondary channel, and a sensor 239 operating over a sensing region 235. Cells may be introduced into the sample channel and flow through the channel to the sensing region 235. The sensor 239 operating over the sensing region 235 may then collect and provide data to the measurement device, including to a classifier, to identify the cell and determine its velocity through the channel. Once a cell is identified, the flow of fluid in the sample channel and the secondary channel may be controlled in order to control the flow of the cell from the sample channel into the secondary channel. Moreover, controlling the flow helps assured that a determined velocity remains consistent for a particular cell, which allows a more accurate projected time for when the cells pass by either the SMR or sensing region. The classifier may identify cells using signals from a sensor 239, frequency data from a resonator, or any other method for discriminating between particles.

When the classifier uses signals from a sensor 239, the sensor may be an imaging sensor, and may comprise an array of sensor elements. Sensor elements may include photoelectric sensor elements. Imaging sensors collect data about light or diffraction patterns incident upon sensor elements from a cell in the sensing region 235. Upon receiving a signal to capture an image from the sensing region 235, incoming light from individual cells and/or particles of cellular and non-cellular material reach an array of sensor elements of the imaging sensor. Each sensor element may collect and store photons from light as an electrical signal. By having an array of sensor elements configured to capture the individual cells and/or particles of cellular and non-cellular material, the imaging sensor can record a present state of the sensing region 235 for the classifier. When sensing color images, the imaging sensor may have a color filter array (CFA) that limits each sensor element to only collect incoming light for a particular color, for example each sensor element may capture light that corresponds to only one primary color.

After light exposure upon the array of sensor elements, the electrical signal from the individual sensor elements may then be used to reproduce the image of the sensing region 235 by configuring the color and brightness of matching pixels to the electrical signals. A computer may be provided to match pixels to recreate the image. In some instances, for every sensor element there may be a corresponding pixel within the recreated image that reflects the charge and color received at the sensor element from the sensing region 235. The classifier may identify cells based on the recreated image of the sensing region 235. The classifier may also identify cells directly from the electrical signals provided by the sensor. In certain aspects, the sensor obtains a plurality of images, and the change in position of the cell within the channel between images is used by the measurement device to calculate flow velocity of a cell.

The imaging sensor may comprise a lens and/or may comprise a camera such as a digital camera. The imaging sensor may be a charge-coupled device (CCD) or may be a complementary metal-oxide-semiconductor (CMOS) sensor. CCD and CMOS sensors can be arranged in a two-dimensional array to capture two-dimensional image signals. Sensor size and/or the number of sensor elements may be used to control the spatial resolution of the image captured. The resolution may be pixel resolution. Increasing the density of sensor elements increases spatial resolution. Increasing the size of sensors increases the amount of light incident on each sensor. Imaging detail may be limited by optics due to lens blurs, lens aberration effects, aperture diffractions, and optical blurring due to motion.

The imaging sensor may advantageously be a lens-free imaging sensor, for example an imaging sensor that does not comprise correction lenses or components. The lens-free imaging may be on chip imaging using a digital optoelectric sensor array, such as a CCD or CMOS chip. Imaging chips and optical components provide the advantage when used with the classifier of capturing very high-resolution images. The chip may directly sample light transmitted through a source without the use of any imaging lenses between the source and the sensor planes. Lens-free imaging sensors can advantageously comprise more compact, lightweight, and simpler hardware than lens-based sensors. Lens-free imaging sensors are described in Greenbaum, 2012, Imaging without lenses: achievements and remaining challenges of wide-field on-chip microscopy, Nat Methods, 9(9):889-895, incorporated by reference.

The classifier may identify cells based on one or more image of the sensing region(s) 235. The image may have a pixel resolution. The classifier may also identify cells directly from electrical signals provided by the sensor elements. The identification of cells by the classifier using data from an imaging sensor may be used to calibrate and optimize cellular measurements in real-time or may be used to calibrate and optimize future measurements from cellular or non-cellular materials.

A classifier may also identify cells using data from a measurement device comprising at least one SMR device 301. Methods for optimized cellular measurement may also comprise the steps of introducing cellular and/or non-cellular particles with overlapping size and/or mass distributions to a measurement device comprising at least one suspended microchannel resonator (SMR) device 301 and identifying the sub-groups of particles in the mixture based on a classifier that utilizes data from said measurement device.

Classification of sub-groups of particles, including cells, using an SMR device 301 may be based on a "node-deviation" signal from an SMR device 301. When measuring deviation of resonant frequency using an SMR device 301, the SMR device 301 acts as an acoustic energy source and scattered acoustic fields from particles provide a signal that is used to monitor mechanical properties of the particles. Vibration of the SMR device 301 varies along the length of a cantilever 333, with one local maximum near the center, referred to as an antinode, and a zero-minimum near the tip, referred to as a node. When cellular or non-cellular particles are at the antinode, the net change in mass of the particle corresponds to the change in kinetic energy of the measurement device, and causes a shift in the resonant frequency of the SMR device 301. As described above, by measuring the frequency at which the cantilever 333 resonates, the instrument computes a mass, density, or change in mass or density, of a cellular and/or non-cellular particle in the fluidic microchannel previously identified by a classifier. When the particle is at the node of the cantilever 333, a net change in mass had previously been theorized not to shift the frequency at which the cantilever 333 resonates because the vibration amplitude is zero and there is no change in kinetic energy. In practice, however, resonant frequency shifts may be consistently measured at the node, including when flowing cells and polystyrene beads through the microfluidic channel. This resonant frequency shift at the node is referred to as node-deviation and corresponds to an energy change due to acoustic scattering from a material's surface dependent on mechanical properties of the material. The SMR device 301 may collect resonant frequency data at the node of cantilever 333 for cellular and non-cellular flowing therethrough. The resonant frequency data from the SMR device 301 may be provided to the classifier and the classifier may identify sub-groups of particles based on a node-deviation of signal from the SMR device 301.

Figure 5:
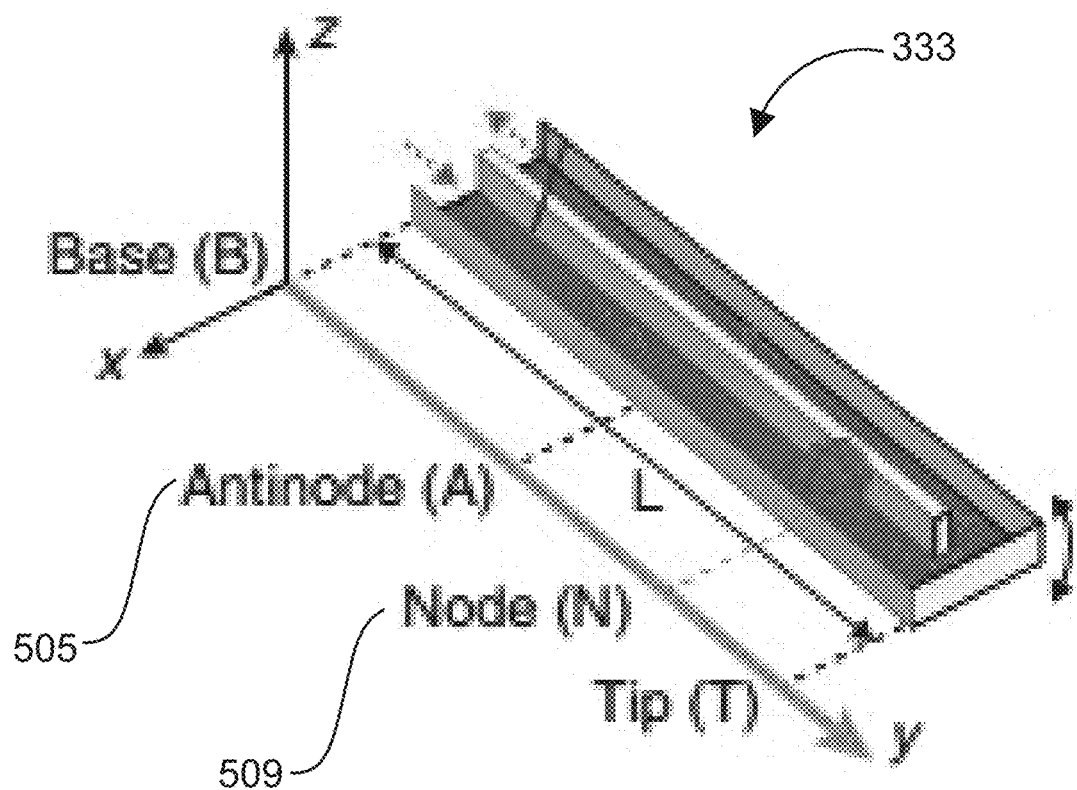
FIG. 5 shows a cantilever of an SMR device.

FIG. 5 shows a cantilever 333 of an SMR 301. When an identified cell is at the antinode 505, the net change in mass of the particle corresponds to the change in kinetic energy of the measurement device, and causes a shift in resonant frequency. By measuring frequency at the antinode 505 the instrument computes the buoyant mass of the cell. When the particle is at the node of the cantilever 509 the resonant frequency shift at the node (the node deviation) corresponds to an energy change due to acoustic scattering from the material's surface dependent on mechanical properties of the cellular or non-cellular particle, such as surface stiffness. Node-deviation data from the SMR device 301 can be provided to a classifier that utilizes the data to identify subgroups of particles, such as different types of cells. The classifier may discriminate between cells, cellular and non-cellular material based on surface stiffness. Non-cellular particles with a known size and/or mass may be used as a reference material to calibrate the measurement device in real-time or calibrate the measurement device for future measurements. Preferably, the reference material has an overlapping size and/or mass with cellular material.

Node-deviation can be measured independently of flow velocity and vibration amplitude. Therefore, by measuring the resonant frequency shifts at the antinode and node as materials flow through the SMR device 301, one can simultaneously and independently quantify the buoyant mass or density of the material and the node deviation for the material. Node deviation may be influenced by a cell's volume. A volume correction may be applied to the measured node-deviation through size-normalized acoustic scattering, with the appropriate correction determined through, for example, finite element method (FEM) simulations for fluid-structure acoustic interactions. Node-deviation may further be influenced by the cell's mass distribution and/or orientation within a microfluidic channel. The mass distribution for a particle of cellular or non-cellular material may be acquired, for example, as bright-field images using a sensor operating over a sensing region or may be known a priori, and a mass distribution correction may be applied to the measured node-deviation. Node-deviation can be used to determine one or more mechanical properties of particles of an identified cell. For example, node deviation may be used to determine surface stiffness of the cell. When measuring node-deviation in a cell, the measurement may be used to determine cell surface stiffness or properties of the actomyosin cortex of the cell. For example, cell surface stiffness varies throughout cell mitosis and node deviation may be used to determine properties and stages of mitosis in the cell. The classifier may identify sub-groups of particles, such as cellular and/or non-cellular particles, based on surface stiffness and/or node-deviation data from an SMR device 301. The identification of sub-groups of particles by the classifier may be used to calibrate and optimize cellular measurements in real-time or may be used to calibrate and optimize future measurements of cellular or non-cellular particles by the measurement device.

The classifier may be based on any suitable machine learning measurement device trained to discriminate between cellular and non-cellular material using data from the sensor operating over the sensor region. For example, the machine learning measurement device may learn in a supervised manner, an unsupervised manner, a semi-supervised manner, or through reinforcement learning.

In supervised learning models, the machine learning measurement device is given training data categorized as input variables paired with output variables from which to learn patterns and make inferences in order to generate a prediction on previously unseen test data. Supervised models replicate an identified mapping measurement device and recognize and respond to patterns in data without explicit instructions. Supervised models are advantageous for performing discrete classification tasks, in which data inputs are separated into categories. Supervised models are also advantageous for continuous regression tasks, in which the output variable is a real value, such as a price or a volume. The accuracy of a supervised model is easy to evaluate because there is a known output variable to which the model is optimizing. Supervised models are advantageous for training a classifier to separate cellular and non-cellular material into respective categories when a suitable training data set for cellular and non-cellular materials is available. For example, a training set comprising labeled images of cellular particles and non-cellular particles may be used by the classifier to identify cellular and non-cellular particles in imaging data provided by an imaging sensor.

In an unsupervised model or autonomous model, the machine learning measurement device is only given input training data without paired output data from which to identify patterns autonomously. Unsupervised models identify underlying patterns or structures in training data to make predictions for test data. Unsupervised models are advantageous for clustering data, anomaly detection, and for independently discovering rules for data. The accuracy of unsupervised models is harder to evaluate because there is no predefined output variable to which the measurement device is optimizing. Autonomous models may employ periods of both supervised and unsupervised learning in order to optimize predictions. Unsupervised models are advantageous for training a classifier to cluster data into clusters when labeled training data is unavailable. The classifier may use additional data to identify each cluster as cellular or non-cellular material. For example, a classifier may identify clusters of data from a signal provided by an imaging sensor. The classifier may use previously collected node-deviation data from an SMR device 301 to identify which clusters identify cellular material and which clusters identify to non-cellular material.

In semi-supervised models, the machine learning measurement device is given training data comprising input variables, with output variable pairs available for only a limited pool of the input variables. The model uses the input variables with output variable pairs and the remaining input training data to learn patterns and make inferences in order to generate a prediction on previously unseen test data. A semi-supervised model may advantageously query the user for additional paired output data based on unpaired data. Semi-supervised models are advantageous for training a classifier to separate cellular and non-cellular material into respective categories when an incomplete training data set for cellular and non-cellular materials is available. For example, a training set comprising labeled images for some cellular particles and some non-cellular particles may be used by the classifier to correctly identify individual cells in an image provided by a sensor 239 while also identifying clusters of data from the image for particles it cannot identify from the training data set.

In a reinforcement learning model, the machine learning measurement device is given neither input variables nor output variables. Rather, the model provides a "reward" condition and then seeks to maximize the cumulative reward condition by trial and error. A reinforcement learning model is a Markov Decision Process. Supervised, unsupervised, semi-supervised, and reinforcement models are described in Jordan and Mirchell, 2015, Machine learning, Trends, perspectives, and prospects, Science 349(6245):255-260, incorporated by reference.

An example of a supervised learning model is a "decision tree." Decision trees are non-parametric supervised learning models that use simple decision rules to infer a classification for test data from the features in the test data. In classification trees, test data take a finite set of discrete values, or classes, whereas in regression trees, the test data can take continuous values, such as real numbers. Decision trees have some advantages in that they are simple to understand and can be visualized as a tree starting at the root (usually a single node) and repeatedly branch to the leaves (multiple nodes) that are associated with the classification. See Criminisi, 2012, Decision Forests: A unified framework for classification, regression, density estimation, manifold learning and semi-supervised learning, Foundations and Trends in Computer Graphics and Vision 7(2-3):81-227, incorporated by reference. Decision tree models can be advantageous for the classifier to identify particles of cellular or non-cellular material because the particles fall into a discrete set of classes or categories, e.g., cellular or non-cellular. For example, the classifier may identify that a cell is in an image provided by a sensor 239 and using training data to infer that the particle is a particular type of cell, such as a cancer cell.

Another supervised learning model is a "support-vector machine" (SVM) or "support-vector network." SVMs are supervised learning models for classification and regression problems. When used for classification of new data into one of two categories, such as whether a particle is cellular or non-cellular, an SVM creates a hyperplane in multidimensional space that separates data points into one category or the other. Although the original problem may be expressed in terms that require only finite dimensional space, linear separation of data between categories may not be possible in finite dimensional space. Consequently, multidimensional space is selected to allow construction of hyperplanes that afford clean separation of data points. See Press, W. H. et al., Section 16.5. Support Vector Machines. Numerical Recipes: The Art of Scientific Computing (3rd ed.). New York: Cambridge University (2007), incorporated herein by reference. Where output variable pairs are unavailable for input variables in the training data, SVMs can be designed as unsupervised or semi-supervised learning models using support vector clustering. See Ben-Hur, 2001, Support Vector Clustering, J Mach Learning Res 2:125-137, incorporated by reference. SVM models can be advantageous for the classifier to identify cells. Additionally, SVM models can be advantageous where only a limited set of training data is available for the classifier.

Logistic regression analysis is another statistical process that can be used by the classifier to find patterns in training and test data to make predictions. It includes techniques for modeling and analyzing relationships between multiple variables. Specifically, regression analysis focuses on changes in a dependent variable in response to changes in single independent variables. Regression analysis can be used to estimate the conditional expectation of the dependent variable given the independent variables. The variation of the dependent variable may be characterized around a regression function and described by a probability distribution. Parameters of the regression model may be estimated using, for example, least squares methods, Bayesian methods, percentage regression, least absolute deviations, nonparametric regression, or distance metric learning. Like SVM models, regression models are also advantageous for the classifier to identify cells. Regression models also provide the advantage of being effectively implemented by a variety of tools and the model can be easily updated to identify new cells.

Bayesian algorithms can also be used to find patterns in training and test data to make predictions. Bayesian networks are probabilistic graphical models that represent a set of random variables and their conditional dependencies via directed acyclic graphs (DAGs). The DAGs have nodes that represent random variables that may be observable quantities, latent variables, node unknown parameters or hypotheses. Edges represent conditional dependencies; nodes that are not connected represent variables that are conditionally independent of each other. Each is associated with a probability function that takes, as input, a particular set of values for the node's parent variables, and gives (as output) the probability (or probability distribution, if applicable) of the variable represented by the node. Like SVM models and regression models, Bayesian models are also advantageous for the classifier to identify cells. Bayesian models provide the advantage of generally requiring less training data than other models and can be used by the classifier to identify individual cells quickly.

Some models rely on clustering training data and test data to find patterns and make predictions. A "k-nearest neighbor" (k-NN) model is a supervised non-parametric learning model for classification and regression problems. A k-nearest neighbor model assumes that similar data exists in close proximity, and assigns a category or value to each data point based on the k nearest data points. k-NN models may be advantageous when the data has few outliers and can be defined by homogeneous features. k-NN models can be advantageous for the classifier to identify particles of cells because the cells fall into a discrete set of classes or categories, e.g., cancer and non-cancer cells. Moreover, k-NN models provide the advantage of continuously learning from test data and do not require a training period before identifying cells from training data.

An example of an unsupervised learning model that uses clustering is a "k-means" clustering model. A k-means model looks to find clusters of data in input data and test data. K-means models are advantageous when a defined number of clusters are known to exist in the data and are also advantageous when the test data has few outliers and can be defined by homogeneous features. Additional models that cluster training data include, for example, farthest-neighbor, centroid, sum-of-squares, fuzzy k-means, and Jarvis-Patrick clustering. k-means and other unsupervised clustering models are advantageous for use by the classifier to identify cells when training data cells is unavailable or limited.

Trained machine learning models can become "stable learners." A stable learner is a model that is less sensitive to perturbation of predictions based on new training data. Stable learners can be advantageous where test data is stable, but can be less advantageous where the measurement device needs to continually improve performance to accurately predict new test data that may be less stable. Accordingly, a stable learning model may be advantageous for use by the classifier when the types of cellular and non-cellular material that may be introduced to the measurement device are known and are unlikely to change.

Several machine learning measurement device types can be combined into a final predictive model (an ensemble). Ensembles can be divided into two types, homogenous ensembles and heterogeneous ensembles. Homogenous ensembles combine multiple machine learning models of the same type. Heterogeneous ensembles combine multiple machine learning models of different types. Ensembles can provide an advantage when used by the classifier to identify cells because they can be more accurate than any of the individual base member models ("members") in the ensemble. The number of members combined in an ensemble may impact the accuracy of a final prediction. Accordingly, it is advantageous to determine the optimal number of members when designing an ensemble measurement device for use by the classifier.

Ensembles used by the classifier may combine or aggregate outputs from individual members by using "voting"-type methods for classification measurement devices and "averaging"-type methods for regression measurement devices. In a "majority voting" method, each member makes a prediction as to the identification of cells in test data and the prediction that receives more than half of the votes is the final output for the ensemble. If none of the predictions receives more than half of the votes, it may be determined that the ensemble is unable to make a stable prediction. In a "plurality voting" method the most voted prediction, even if receiving less than half of the votes, may be considered the final output for the ensemble. In a "weighted voting" method, the votes of more accurate members are multiplied by a weight afforded each member based on its accuracy. In a "simple averaging" method, each member makes a prediction for test data and the average of the outputs is calculated. This method reduces overfit and can be advantageous in creating smoother regression models. In a "weight averaging" method, the prediction output of each member is multiplied by a weight afforded each member based on its accuracy. Voting methods, averaging methods, and weighted methods can be combined to improve the accuracy of ensembles used by the classifier.

Members within an ensemble used by the classifier can each be trained independently, or new members can be trained utilizing information from previously trained members. In a "parallel ensemble", the ensemble seeks to provide greater accuracy than individual members by exploiting the independence between members, for example, by training multiple members simultaneously to identify individual cells and/or cellular and non-cellular material and aggregating the outputs from members. In "sequential ensemble measurement devices", the ensemble seeks to provide greater accuracy than individual members by exploiting the dependence between members, for example, by utilizing information from a first member regarding the identification of individual cells and/or cellular and non-cellular material to improve the training of a second member for identifying individual cells and/or cellular and non-cellular material and weighting outputs from members.

Overall accuracy for ensembles used by the classifier can also be optimized by using ensemble meta-algorithms, for example a "bagging" algorithm to reduce variance, a "boosting" algorithm to reduce bias, or a "stacking" algorithm to improve predictions.

Boosting algorithms reduce bias and can be used to improve less accurate, or "weak learning" models. A member may be considered a "weak learning" model if it has a substantial error rate, but its performance is non-random, for example an error rate of 0.5 for classifying a particle as cellular or non-cellular. Boosting algorithms incrementally build the ensemble by training each member sequentially with the same training data set, examining prediction errors for test data (i.e., labeling a cell as a non-cellular particle), and assigning weights to training data based on the difficulty for members to make an accurate prediction. In each sequential member trained, the algorithm emphasizes training data that previous members found difficult. Members are then weighted based on the accuracy of their prediction outputs in view of the weight applied to the training data. The predictions from each member may be combined by weighted voting-type or weighted averaging-type methods. Boosting algorithms are advantageous when combining multiple weak learning models. Boosting algorithms may, however, result in over-fitting test data to training data. Examples of boosting algorithms include AdaBoost, gradient boosting, eXtreme Gradient Boost (XGBoost). See Freund, 1997, A decision-theoretic generalization of on-line learning and an application to boosting, J Comp Sys Sci 55:119; and Chen, 2016, XGBoost: A Scalable Tree Boosting Measurement device, arXiv:1603.02754, both incorporated by reference.

Bagging algorithms or "bootstrap aggregation" algorithms reduce variance by averaging together multiple estimates from members. Bagging algorithms provide each member with a random sub-sample of a full training data set, with each random sub-sample known as a "bootstrap" sample. In the bootstrap samples, some data from the training data set may appear more than once and some data from the training data set may not be present. Because sub-samples can be generated independently from one another, training can be done in parallel. The predictions for test data from each member are then aggregated, such as by voting-type or averaging-type methods.

An example of a bagging algorithm that may be used by the classifier to identify individual cells and/or cellular and non-cellular material is a "random forest" algorithm. In a random forest the ensemble combines multiple randomized decision tree models. Each decision tree model is trained from a bootstrap sample from a training set for identifying individual cells and/or cellular and non-cellular material. The training set itself may be a random subset of features from an even larger training set. By providing a random subset of the larger training set at each split in the learning process, spurious correlations that can results from the presence of individual features that are strong predictors for the output variable are reduced. By averaging predictions for test data, variance of the ensemble decreases resulting in an improved prediction to identify individual cells and/or cellular and non-cellular material. Random forests may be autonomous models and may include periods of both supervised and unsupervised learning. Bagging may be less advantageous in optimizing an ensemble combining stable learning measurement devices, since stable learning measurement devices tend provide generalized outputs with less variability over the bootstrap samples. Random forests are advantageous for use by the classifier to identify individual cells and/or cellular and non-cellular material by providing a great degree of versatility in identifying individual cells and/or cellular and non-cellular material and reducing spurious identification by the classifier. See Breiman, 2001, Random Forests, Machine Learning 45:5-32, incorporated by reference.

Stacking algorithms or "stacked generalization" algorithms improve predictions by using a meta-machine learning model to combine and build the ensemble. In stacking algorithms, base member models are trained with a training dataset and generate as an output a new dataset. This new dataset is then used as a training dataset for the meta-machine learning model to build the ensemble. Stacking algorithms are generally advantageous for use by the classifier to identify individual cells and/or cellular and non-cellular material when building heterogeneous ensembles. Ensembles are described in Villaverde et al., 2019, On the adaptability of ensemble methods for distribution classification measurement devices: A comparative analysis, International Journal of Distributed Sensor Networks 15(7); and Heitor et al., 2017, A Survey of Ensemble Learning for Data Stream Classification, 50(2):Art. 23, each incorporated by reference.

Neural networks, modeled on the human brain, allow for processing of information and machine learning. The classifier for identifying individual cells and/or cellular and non-cellular material may advantageously be based on a neural network. Neural networks include nodes that mimic the function of individual neurons, and the nodes are organized into layers. Neural networks include an input layer, an output layer, and one or more hidden layers that define connections from the input layer to the output layer. Measurement devices and methods of the invention may include any neural network that facilitates machine learning. The measurement device may include a known neural network architecture, such as GoogLeNet (Szegedy, et al. Going deeper with convolutions, in CVPR 2015, 2015); AlexNet (Krizhevsky, et al. Imagenet classification with deep convolutional neural networks, in Pereira, et al. Eds., Advances in Neural Information Processing Measurement devices 25, pages 1097-3105, Curran Associates, Inc., 2012); VGG16 (Simonyan & Zisserman, Very deep convolutional networks for large-scale image recognition, CoRR, abs/3409.1556, 2014); or FaceNet (Wang et al., Face Search at Scale: 80 Million Gallery, 2015), each of the aforementioned references are incorporated by reference. The advantage of using a classifier to identify individual cells and/or cellular and non-cellular material based on a neural network architecture is that neural networks are able to learn patterns and correlations by themselves and produce outputs that are not limited to the training data provided to them. The neural network architecture allows the classifier to learn from examples of individual cells and/or cellular and non-cellular particles and identify new particles in real-time. Additionally, the neural network architecture allows the classifier to identify multiple particles in parallel as they flow through a measurement device. For example, a classifier based on a neural network architecture may be provided image data from an image sensor 239 and identify and track individual cells in real time with increasing accuracy as the number of images provided to the classifier increases.

Deep learning neural networks (also known as deep structured learning, hierarchical learning or deep machine learning) include a class of machine learning operations that may be used by the classifier that use a cascade of many layers of nonlinear processing units for feature extraction and transformation. Each successive layer uses the output from the previous layer as input. The algorithms may be supervised or unsupervised and applications include pattern analysis (unsupervised) and classification (supervised). Certain embodiments are based on unsupervised learning of multiple levels of features or representations of the data. Higher level features are derived from lower-level features to form a hierarchical representation. Deep learning by the neural network includes learning multiple levels of representations that correspond to different levels of abstraction; the levels form a hierarchy of concepts. In some embodiments, the neural network includes at least 5 and preferably more than ten hidden layers. The many layers between the input and the output allow the measurement device to operate via multiple processing layers. For example, a classifier based on a deep learning neural network may be provided image data from an imaging sensor. Earlier hidden layers in the network may identify the edges of cells and their location in the image with later hidden layers identifying the brightness of each cell. The two features together may be used by a further hidden later to provide an output prediction for each cell in the image to the classifier.

Within a neural network that may be used by the classifier, nodes are connected in layers, and signals travel from the input layer to the output layer. Each node in the input layer may correspond to a respective feature from the training data for individual cells and/or cellular and non-cellular material. The nodes of the hidden layer are calculated as a function of a bias term and a weighted sum of the nodes of the input layer, where a respective weight is assigned to each connection between a node of the input layer and a node in the hidden layer. The bias term and the weights between the input layer and the hidden layer are advantageously learned autonomously in the training of the neural network. The network may include thousands or millions of nodes and connections. Typically, the signals and state of artificial neurons are real numbers, typically between 0 and 1. Optionally, there may be a threshold function or limiting function on each connection and on the unit itself, such that the signal must surpass the limit before propagating. Back propagation is the use of forward stimulation to modify connection weights, and is sometimes done to train the network using known correct outputs. See WO 2016/182551, U.S. Pub. 2016/0174902, U.S. Pat. No. 8,639,043, and U.S. Pub. 2017/0053398, each incorporated by reference.

An image from an imaging sensor provided to a classifier can be represented by a deep learning network in many ways, such as a vector of intensity values per pixel in the image, or in a more abstract way as a set of edges, regions of particular shape, etc. Those features are represented at nodes in the network. Preferably, each feature is structured as numerical feature or vector that represents the image feature. This provides a numerical representation of objects in the image since such representations facilitate processing and statistical analysis. Numerical features are often combined with weights using a dot product in order to construct a linear predictor function that is used to determine a score for making a prediction.

The vector space associated with those feature vectors may be referred to as the feature space. In order to reduce the dimensionality of the feature space, dimensionality reduction may be employed by networks used by the classifier. Higher-level features can be obtained from already available features and added to the feature vector, in a process referred to as feature construction. Feature construction is the application of a set of constructive operators to a set of existing features resulting in construction of new features. For example, a classifier based on a neural network architecture may be provided image data from an image sensor. Early layers in the neural network may identify horizontal lines and vertical lines in the image data. Later layers in the network may then use the lines identified to obtain edges, a higher-level feature, for individual cells in the image.

A convolutional neural network (CNN) is a class of deep neural network generally designed for two-dimensional image inputs in which a signal travels from the input layer through hidden layers comprising "convolutional layers" and "fully connected layers" to the output layer. Accordingly, a CNN is particularly advantageous for use by the classifier when provided image inputs, for example from an imaging sensor. In the input layer of a CNN, each pixel from an image is mapped. The input layer is connected to a convolutional layer. In a convolutional layer, each node is "sparsely connected", that is connected to only a sub-matrix of pixels or nodes from the previous layer. The connection between the submatrix of nodes and the convolutional layer is subject to a bias term as a set of weights designed detect a given feature in the input. The submatrix and weights together are known as a "filter," "kernel," or "feature detector". For a given convolutional layer, each filter is the same size and shape and applies the same set of weights. Each node in the convolutional layer is provided a summary of the weighted information from the filter as a scalar dot product. The filters are staggered from one another and may overlap such that each node in convolution layer provides a weighted summary for a different sub-matrix from the previous layer. A threshold function may be applied to each node in the convolution layer to determine whether the node will propagate the information from the filter, a function known as "squashing."

Sliding the filter across the entire input allows the filter to discover a given feature anywhere in the input. This provides the advantage of allowing a classifier based on a CNN to identify individual cells anywhere in imaging data provided to the classifier. The function of sliding the filter over the entire image can be controlled by the number of nodes over which the filter passes, known as the "stride" of the convolutional layer. The stride determines the distance that each filter is staggered from adjacent filters and the degree of overlap between filters. The final two-dimensional array of dot products of the convolutional layer is known as the "convolved feature," "activation map," or "feature map."

Filters may also have a given depth. For example, color images have multiple channels, typically one for each color channel, such as red, green, and blue. This means that a single color image provided as an input to the input layer is, in fact, three images. A filter must always have the same number of channels as the input, referred to as "depth". If an input image has 3 channels then a filter applied to that image must also have 3 channels, resulting in, for example, each 2×2 filter becoming a 2×2×3 filter (length×width×depth). Regardless of the depth of the input and depth of the filter, the filter is applied to the input using a dot product operation which results in a single value. This means that if a convolutional layer has 32 filters, these 32 filters are not just two-dimensional for the two-dimensional image input, but are also three-dimensional, having specific filter weights for each of the three channels. Each filter contributes to a single feature map. Accordingly, a classifier based on a CNN may be advantageous where the data provided to the classifier comprises color images and/or inputs with multiple channels.

Different filters produce different feature maps. A convolutional layer may apply a different filter depending on the given input, with the types of filters available learned during training of the network. For example, the network may be trained to apply filters for a specific task the network is trained to resolve, such as detecting whether an input image contains a vertical line. The convolution layer may be trained to apply any number of possible filters to an input image.

In some instances, it may also be convenient to "pad" an input to a convolutional layer with zero values around the border of the input, a process known as zero-padding. Zero-padding allows the size of feature maps to be controlled. This can allow for the feature map to remain the same size as the input through multiple layers of the CNN. The function of adding zero-padding is known as "wide-convolution" versus "narrow convolution" when no zero-padding is added.

The use of multiple convolutional layers in the network allows for hierarchical decomposition of the input. Convolutional filters that operate directly on input values may learn to extract low level features, such as lines. Convolutional filters that operate on the output from earlier convolution layers may learn to extract features that are combinations of lower-level features, such as features that comprise multiple lines to express shapes. The classifier can use multiple convolution layers to reconstruct particles from an input and thereafter identify individual cells.

A CNN used by a classifier may also comprise nonlinear layers (ReLU). A ReLU layer receives a feature map and replaces any negative values in the feature map with a zero. The purpose of the ReLU layer is to introduce non-linearity into the CNN and is advantageous when the input data that the CNN is expected to learn and identify is non-linear, including image features such as particles. The non-linear output map from a ReLU is known as a "rectified" feature map. The CNN may also comprise pooling layers. A pooling layer reduces the size of the feature map or rectified feature map through dimensionality reduction in a process known as "spatial pooling," "subsampling," or "down sampling." For example, each node in a pooling layer may be sparsely connected to a sub-matrix of nodes from a convolution or ReLU layer. Each node in the pooling layer may then provide, for example, only the highest value, average of, or sum of the values in each submatrix. Pooling layers can be advantageous to make input representations smaller and more manageable, reduce the number of parameters and computations in the network, reduce the impact of distortions in the input image, and/or help scale representation of the image. This provides the advantage of reducing training time and controlling overfitting in the CNN used by the classifier to identify and track individual cells. The final output from the convolutional, ReLU, and/or pooling layers, for example the extraction of particle features from imaging data, is provided to a fully connected layer. The fully connected layers operate under the same principles as a traditional neural network. In a fully connected layer, each node in the layer is connected to all of the nodes in a previous layer and all of the nodes in a succeeding layer. The purpose of a fully connected layer is to classify the features extracted by the convolutional layers, for example using single vector machines (SVM) to classify the particle features extracted by the previous layers. Backpropagation in CNNs involves adjusting the weights of filters based on the error rate of the CNN, known as "loss." During backpropagation, the CNN determines the estimated loss at every node in each convolutional layer and adjusts filter weights accordingly to minimize loss. A CNN may be trained by multiple rounds of backpropagation. Convolutional Neural Networks are described in Haridas and Jyothi, 2019, Convolutional Neural Networks: A Comprehensive Survey, 14(3):780-789, incorporated by reference. CNNs are advantageous for use with the classifier for identifying and track individual cells because they provide automatic feature extraction from input data and autonomously learn the features necessary to allow the classifier to identify and track individual cells.

The classifier of the present invention may comprise a neural network architecture trained to use sensor 239 data to identify individual cells. For example, the classifier may comprise a convolutional neural network (CNN). Identification of cells (and non-cellular materials) allows for control of flow of fluid through the measurement device, allowing for optimized cellular measurement, for example mass or density accumulation rate. The classifier may advantageously identify individual cells. The classifier may also identify individual cells and/or cellular and non-cellular material or sub-groups of particles and the identification may be used to calibrate the measurement device for future measurements.

The classifier may be trained using data from a measurement device previously obtained from different sub-groups of particles or cells. The sub-group of particles may comprise individual cells and/or cellular and/or non-cellular material. The classifier may be trained by backpropagation using data from a measurement device previously obtained from the sub-groups of cells and/or non-cellular material. The classifier may be trained using a training data set comprising imaging data, for example from an imaging sensor. The classifier may be trained using resonant frequency data, for example node-deviation.

The identification of individual cells in the device allows for the selective flow of cellular and/or non-cellular material from the sample channel into the secondary channel. By controlling the flow of cellular and non-cellular material into the secondary channel, cellular and non-cellular materials can be loaded into the secondary channel at a specified ratio. Cellular and non-cellular materials may be loaded into the secondary channel at a ratio, for example, such that non-cellular reference material periodically flows into the second channel to recalibrate measurements for cellular material or to recalibrate the measurement device. Designation of cellular or non-cellular material may be paired with the respective measurements collected for cellular or non-cellular material. The measurements collected for cellular and non-cellular material may be, for example, mass, density, or MAR. The measurements may be collected by an SMR device 301. The identification of particles of cellular and non-cellular materials or sub-groups of particles may be in real time, for example, where the particles flow through a device and data is collected from the particles and the classifier identifies the particles based on the data as the particles flow through the device. Data may also be collected from the particles and later provided to a classifier which identifies the particles, with the data used for training a classifier or for calibrating the measurement device.

Cellular material can include cellular material selected from the group consisting of cells, cell aggregates, exosomes, extracellular vesicles, cellular components, cellular fragments, organelles, organoids, proteins and protein aggregates, DNA, and RNA. Cells can comprise any biological cells, such as bacterial cells or mammalian cells. Mammalian cells, for example, can include cancer cells, such as tumor cells, glioblastoma cells, or leukemia cells. Mammalian cells can also include immune cells and cancer related immune cells including T cells such as CD8+T cells. Cells can also be living cells. The classifier 255 may identify the cellular material as a specific type of cellular material, for example, cells, cell aggregates, exosomes, extracellular vesicles, cellular components, cellular fragments, organelles, organoids, proteins and protein aggregates, DNA, and RNA. Notably, methods of the invention analyze the sample without destroying the cells. The advantage of using living cells is that the cells are available for further analysis, such as genome sequencing, flow cytometry, or other measurements.

Non-cellular material can include material selected from the group consisting of synthetic particles, inorganic particles, and debris. The classifier 255 may identify the non-cellular material as a specific type of non-cellular material, for example synthetic particles, inorganic particles, or debris. Non-cellular material may include reference material with a known property. The known property of the reference material may be size, mass, and/or density. The reference material may be a synthetic particle and the synthetic particle may be a bead. Beads may be microspheres and may have a known property, such as size, mass, and/or density for use as a reference material for calibrating measurements or measurement devices. For example, beads may have a known mass which can be used to calibrate a measurement device prior to taking measurements or may be used to adjust measurements that have been previously made. Beads may be selected to approximate the size, emission wavelength, and intensity of a biological sample. Beads may include polystyrene beads or silica beads. Debris, such as cell debris, may also be included in a sample. Debris once identified may be rejected from entering or removed from the measurement device. Debris may also be loaded with the sample into the measurement device and any measurements from debris excluded.

Cellular and non-cellular material may be introduced into the measurement device separately or together in the same sample. For example, the cellular and non-cellular material may be introduced together into the sample channel as a single fluid or as separate fluids. A sensor 239 operating over the sensing region 235 provides data to a classifier that utilizes the data to control flow in the sample and secondary channels based on the identification of an individual cell and/or non-cellular material in the fluid or fluids. For example, cells and polystyrene beads may be introduced into the measurement device at the same time and the classifier may identify the cells as cells and the polystyrene beads as polystyrene beads. Loading cells together with polystyrene beads provides the advantage of allowing real-time density estimates of the fluid where cells and beads flow together through the device. Once identified, particles of cellular and/or non-cellular material may additionally be introduced into the secondary channel and/or into a measurement device at different flow rates optimized for measuring one or more properties of the cells and/or non-cellular material, for example mass or mass accumulation rate.

Figure 6:
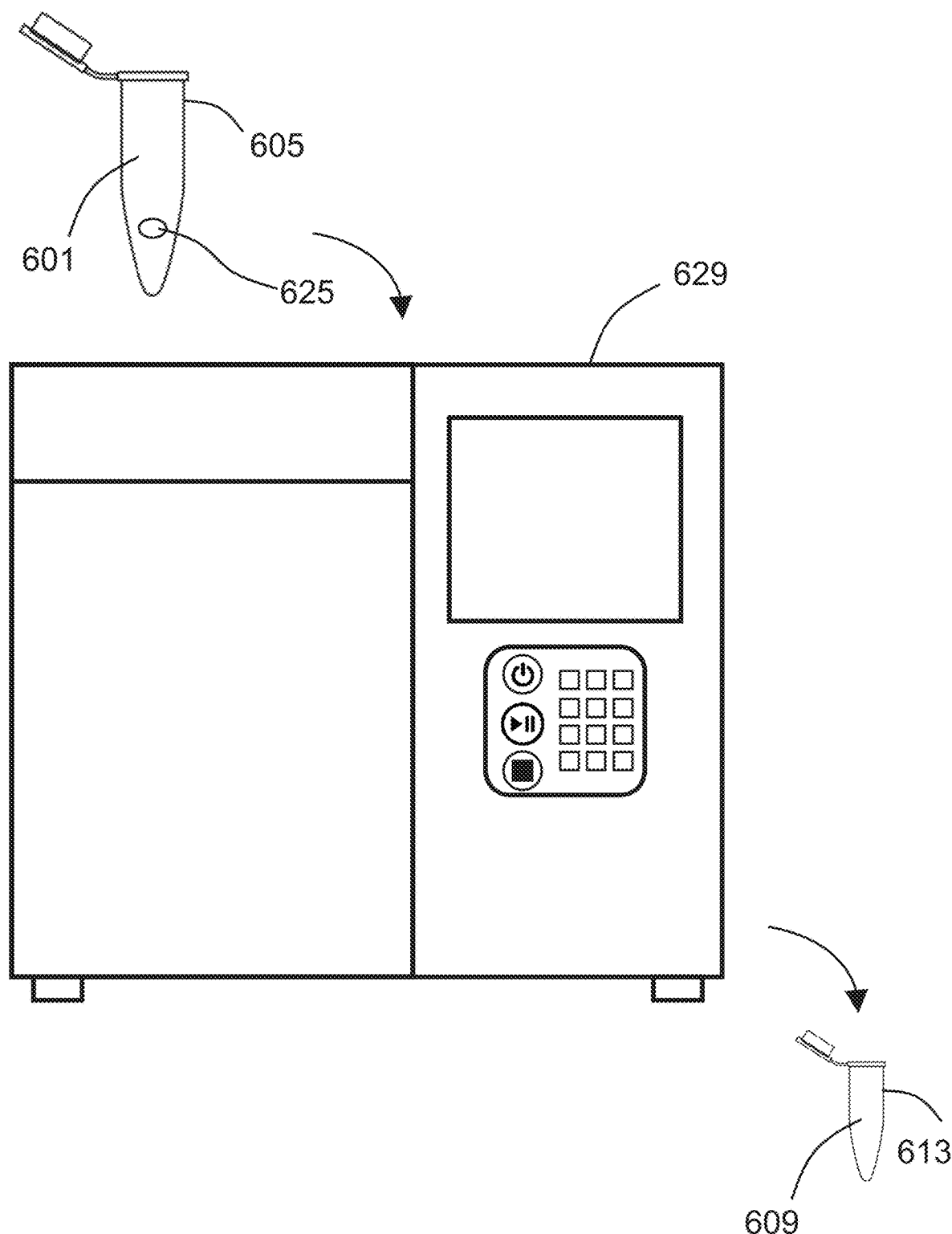
FIG. 6 shows loading live cells into an instrument for an optimized cellular measurement.

FIG. 6 shows introducing 129 a sample 601 comprising cellular and or non/cellular material 625 into an instrument 629 capable of making 651 optimized cell measurements 625. The sample 601 may include one or more live cells, such as a cancer cell or an immune cell. Samples may be collected and stored in their own container 605, such as a tube or flask such as the 1.5 mL micro-centrifuge tube sold under the trademark EPPENDORF FLEX-TUBES by Eppendorf, Inc. (Enfield, Conn.). The instrument 629 is operable to make optimized cell measurements in the one or more live cells, such as single-cell biophysical properties, including, but not limited to, mass, density, growth rate, and mass accumulation of an individual living cell using an SMR in the instrument. These measurements may be correlated by the instrument with the identity of an individual cells as determined by another sensor of the instrument.

The instrument 629 may use a classifier that uses data from a sensor or from a suspended microchannel resonator (SMR) device 301 to identify and control the flow of individual cells though the device, such as through a sample channel 229 and a secondary channel 269. Cells may be loaded into a secondary channel for measurement by the SMR device 301. The SMR device 301 may be used to precisely measure biophysical properties, such as mass and density and/or mass and density changes, of a single cell flowing therethrough. The mass change may be mass accumulation rate (MAR). Upon passing through the instrument 629, single cells remain viable and can be isolated downstream from the instrument 629 and are available to undergo subsequent assays. As shown, a sample 609 of the one or more live cells having undergone the first assay (i.e., passing through the instrument 629) are collected in a suitable container 613 and are then available to undergo a second assay.

The mass accumulation, density accumulation, and/or rates of mass/density accumulation can be a clinically important property that is used to indicate the presence of cancer cells or the efficacy of a therapeutic on cancer cells. Cancer cells may be obtained from a patient and introduced into the measurement device of the present invention for an optimized cell measurement. Cells may be from a biological sample obtained from a patient by any suitable means. Examples of obtaining the sample include fine needle aspiration, blood draw, and biopsy.

Fine needle aspiration and bone marrow biopsy provide a solid biological sample from the patient, providing the ability to sample from pleural effusions and ascites. Accordingly, the sample does not need to be in liquid form. Solid biological samples, for example from fine needle aspiration, may preferably be disaggregated and/or added to a buffer prior to introduction to the instrument. Accordingly, optimized cellular measurements may be obtained from cells from a tissue sample obtained from a solid tumor and the tumor can be from one selected from the group consisting of a bone, bladder, brain, breast, colon, esophagus, gastrointestinal tract, urinary tract, kidney, liver, lung, nervous measurement device, ovary, pancreas, prostate, retina, skin, stomach, testicles, and uterus of a subject. The methods may be used to obtain tumors or cancers of any suitable type. Methods may include accessing a tumor in a patient via fine needle aspirate to take a biological sample comprising cancer cells, disaggregating the biological sample to isolate at least one living cell. The solid biological sample may then be suspended in a media and introduced to the measurement instrument. Non-limiting examples of media include saline, nutrient broth, and agar medium. Examples of biopsies that may provide cells for optimized cellular measurement using measurement devices and methods described herein can include, needle biopsy, bone biopsy, bone marrow biopsy, liver biopsy, kidney biopsy, aspiration biopsy, prostate biopsy, skin biopsy, or surgical biopsy.

A tissue sample may include a mass of connected cells and/or extracellular matrix material, e.g. skin tissue, hair, nails, nasal passage tissue, CNS tissue, neural tissue, eye tissue, liver tissue, kidney tissue, placental tissue, mammary gland tissue, placental tissue, mammary gland tissue, gastrointestinal tissue, musculoskeletal tissue, genitourinary tissue, bone marrow, and the like, derived from, for example, a human or other mammal and includes the connecting material and the liquid material in association with the cells and/or tissues.

Liquid material derived from, for example, a human or other mammal such as body fluids may also be utilized. Such body fluids include, but are not limited to, mucous, blood, plasma, serum, serum derivatives, bile, blood, maternal blood, phlegm, saliva, sputum, sweat, amniotic fluid, menstrual fluid, mammary fluid, follicular fluid of the ovary, fallopian tube fluid, peritoneal fluid, urine, semen, and cerebrospinal fluid (CSF), such as lumbar or ventricular CS. A sample also may be media containing cells or biological material. A sample may also be a blood clot, for example, a blood clot that has been obtained from whole blood after the serum has been removed. In certain embodiments, the sample is blood, saliva, or semen collected from the subject.

Any suitable sample may be obtained for optimized cellular measurements by the methods and measurement devices of the invention. For example, the sample may include immune cells or cancer cells. The sample may include tissue of any type including healthy tissue or bodily fluid of any type. In some embodiments, the tissue sample is obtained from a pleural effusion in a subject. A pleural effusion is excess fluid that accumulates in the pleural cavity, the fluid-filled space that surrounds the lungs. This excess fluid can impair breathing by limiting the expansion of the lungs. Various kinds of pleural effusion, depending on the nature of the fluid and what caused its entry into the pleural space, may be sampled. A pneumothorax is the accumulation of air in the pleural space, and is commonly called a "collapsed lung". In certain embodiments, the tissue sample is obtained from ascetic fluid in a subject. Ascites is the accumulation of fluid (usually serous fluid which is a pale yellow and clear fluid) that accumulates in the abdominal cavity. The abdominal cavity is located below the chest cavity, separated from it by the diaphragm. The accumulated fluid can have many sources such as liver disease, cancers, congestive heart failure, or kidney failure.

The biological sample may include a fine needle aspirate or a biopsy from a tissue known to be, or suspected of being, cancerous. The sample may include a bodily fluid from a patient either known to include, or suspected of including, cancer cells or cancer-related cells (i.e., immune cells).

Accordingly, the cancer cell may be from a patient having or suspected of having a cancer. Types of cancer are characterized by the cells from which they originate. Cancer types include carcinomas such as breast, prostate, lung, pancreatic, and colon cancers that arise from epithelial cells. Sarcomas are derived from connective tissue (e.g., bone, cartilage, fat, or nerve cells). Lymphoma and leukemia arise from hematopoietic cells and are found in the lymph nodes and blood of afflicted patients. Cancer of plasma cells (myeloma) is another cancer found in blood. Germ cell cancers derived from pluripotent cells and blastomas from precursor cells or embryonic tissue are other types of cancer. Cancers may be categorized by those detectable in body fluids, for example, lymphoma, leukemia, or multiple myeloma, as well as those detectable in solid tumors, for example carcinomas or sarcomas. Optimized measurements of the present measurement devices and methods may be used to measure cancers detectable in body fluids or cancers detectable in solid tumors. Accordingly, the cancer may be a leukemia, a lymphoma, a myeloma, a melanoma, a carcinoma, or a sarcoma. In certain embodiments, the cancer involves a solid tumor of, for example, the esophagus, kidneys, uterus, ovaries, thyroid, breast, liver, gallbladder, stomach, pancreas, or colon.

Optimized measurements of individual cells for properties, such as mass and density changes measured in cells, can reveal, for example, if the cells are growing, stationary, or atrophying. Those features of cellular life may be hallmarks of health, cancer, or drug response, and thus methods and devices of the disclosure are valuable tools for precision medicine. Precision Medicine refers to the tailoring of medical treatment to individual characteristics of a patient and the ability to classify individuals into subpopulations that differ in their susceptibility to a particular disease or treatment. Precision medicine often involves genomic or molecular analysis of an individual patient's disease at the molecular level and the selection of targeted treatments to address that individual patient's disease process. In theory, therapeutic interventions are concentrated on those who will benefit, sparing expense and side effects for those who will not. Historically, next-generation sequencing (NGS) technologies make up the core of precision medicine. Clinicians use NGS technologies to screen for cancer-associated mutations or to study gene expression levels. Now, when coupled with existing approaches based on next-generation sequencing, functional measurements according to the invention provide for multi-dimensional precision medicine with benefits in disease areas such as oncology.

Methods and devices of the invention may be used to identify malignant cancer cells in a blood or tissue sample from a patient. Those tools may also be used as an ex vivo test of drug response, useful for therapeutic selection. For example, optimized measurement of MAR in cells provides a measure of cancer in a patient. After treatment of a patient, optimized cellular measurements may be used to monitor recurrence, remission, or relapse. Thus, the invention provides for the improvement of patient care, greater chances of successful cancer treatment, and increased patient life spans. Cancer cells may be obtained from a patient treated for cancer, and the measurement of MAR by the methods and devices of the invention may be used to monitor the effectiveness of the cancer treatment.

Methods and devices of the disclosure are useful for precisely and rapidly measuring growth rates of living individual cells using a small amount of a sample. Only a small amount of a sample may be used to observe and measure a single cell, as opposed to observing a population of cells in traditional methods. Therefore, a small amount of cells can be obtained directly from a subject, suspended in media, and then introduced to a measurement instrument without the need to add additional time-consuming steps, such as culturing the cells. In the invention, the cells from the biological sample are separated when flowing through a microfluidic channel of the measurement instrument and the growth rate of individual cells is measured.

A small sample size may be required as compared to sample sizes necessary in other measurement methods. For example, the sample may comprise about 500 or fewer cells. A small amount of cells may be used because of the precision of the methods of measurement. Therefore, the optimized measurement of the present invention may be advantageous when limited tissue samples are available for testing and measurement. For example, a tissue sample may comprise about 10,000 cells. Such a tissue sample does not have enough cells present in the sample for traditional measurement methods, such as optics measurement methods. Therefore, because 500 or fewer cells may be used, if a sample of about 10,000 cells is provided 20 different test conditions may be tested. For example, 500 cells may be dosed with a first drug to determine the effects of the drug on mass accumulation rate of the cells. Therefore, as many as 20 different drugs may be tested with a sample containing 10,000 cells.

Figure 7:
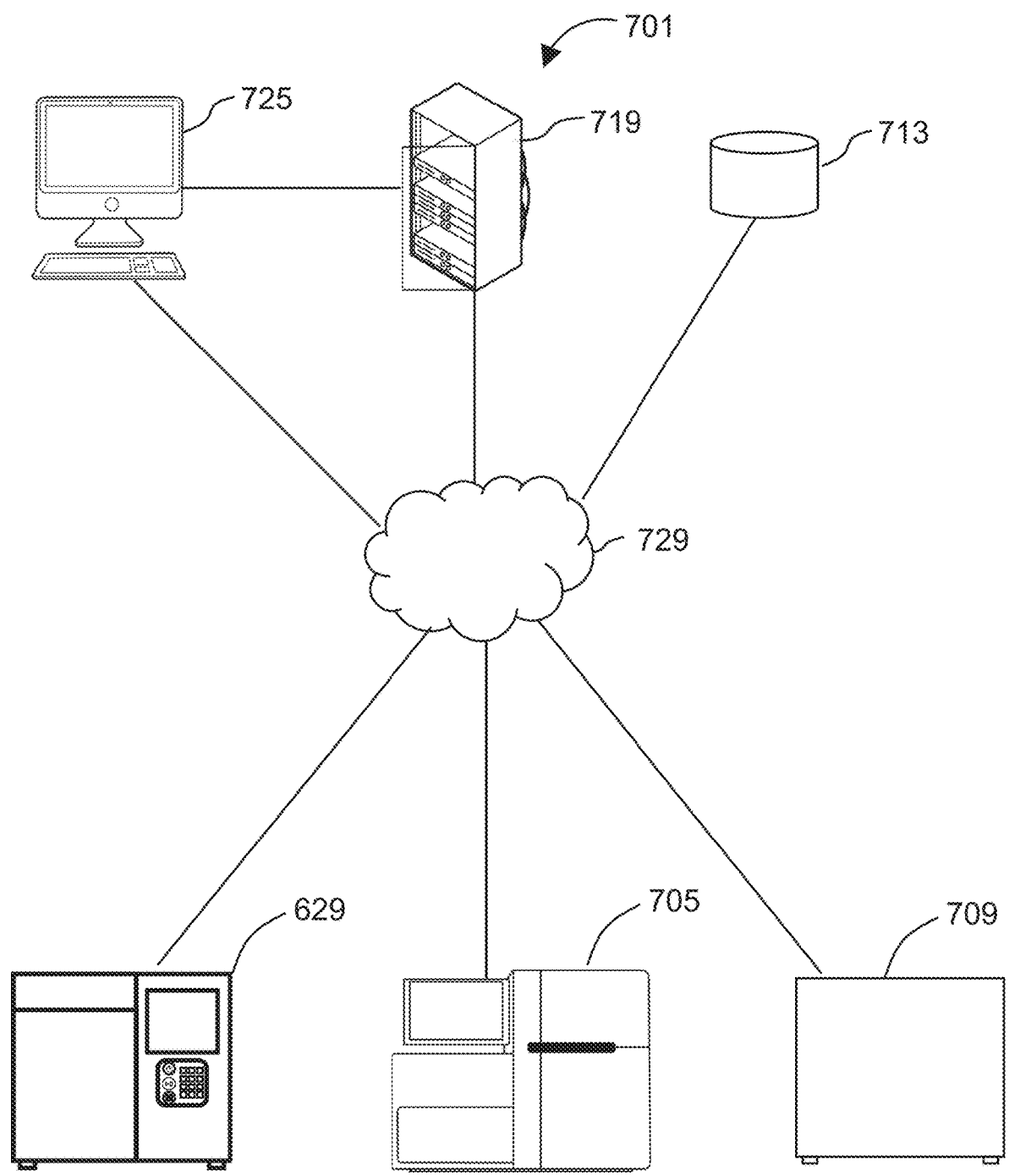
FIG. 7 shows a measurement device useful for performing methods of the disclosure.

FIG. 7 shows an exemplary measurement device 701 useful for performing methods of the disclosure. Preferably, the measurement device provides an instrument 629 capable of making optimized cell measurements and at least one computer 725. The measurement device 701 also preferably includes at least one server 719. The instrument includes a sensor 239 which provides data to a classifier 255 and an SMR 301. The classifier may operate in real-time, and the identification individual cells may be used to control flow through the instrument 629. Either or both of the computer 725 and the server 719 may include and provide the classifier 255. The measurement device 701 may optionally also include any one or more of a storage 713, a sequencing instrument 705, and any additional analysis instruments 709 for performing additional assays on the one or more cells downstream of the initial multimodal measurements obtained by the instrument.

Any of those elements may interoperate via a network 729. Any one of the instruments may include its own built-in or connected computer which may connect to the network 729 and/or the server 729. The instrument 629, for example, may have its own computer or server which provides the classifier 255. The computer 725 may include one or more processors and memory as well as an input/output mechanism. Where methods of the invention employ a client/server architecture, steps of methods of the invention may be performed using the server 729, which includes one or more of processors and memory, capable of obtaining data, instructions, etc., or providing results via an interface module or providing results as a file. The server 719 may be provided by a single or multiple computer devices, such as the rack-mounted computers sold under the trademark BLADE by Hitachi. The server 719 may be provided as a set of servers located on or off-site or both. The server 719 may be owned or provided as a service. The server 719 or the storage 713 may be provided wholly or in-part as a cloud-based resources such as Amazon Web Services or Google. The inclusion of cloud resources may be beneficial as the available hardware scales up and down immediately with demand. The actual processors—the specific silicon chips—performing a computation task can change arbitrarily as information processing scales up or down. In an embodiment, the server 619 includes one or a plurality of local units working in conjunction with a cloud resource (where local means not-cloud and includes or off-site). The server 719 may be engaged over the network 729 by the computer 725.

In the measurement device 701, each computer preferably includes at least one processor coupled to a memory and at least one input/output (I/O) mechanism. A processor will generally include a chip, such as a single core or multi-core chip, to provide a central processing unit (CPU). A processor may be provided by a chip from Intel or AMD.

Memory can include one or more machine-readable devices on which is stored one or more sets of instructions (e.g., software) which, when executed by the processor(s) of any one of the disclosed computers can accomplish some or all of the methodologies or functions described herein. The software may also reside, completely or at least partially, within the main memory and/or within the processor during execution thereof by the computer measurement device. Generally, each computer includes a non-transitory memory such as a solid-state drive, flash drive, disk drive, hard drive, etc. While the machine-readable devices can in an exemplary embodiment be a single medium, the term "machine-readable device" should be taken to include a single medium or multiple media (e.g., a centralized or distributed database, and/or associated caches and servers) that store the one or more sets of instructions and/or data. These terms shall also be taken to include any medium or media that are capable of storing, encoding, or holding a set of instructions for execution by the machine and that cause the machine to perform any one or more of the methodologies of the present invention. These terms shall accordingly be taken to include, but not be limited to one or more solid-state memories (e.g., subscriber identity module (SIM) card, secure digital card (SD card), micro-SD card, or solid-state drive (SSD)), optical and magnetic media, and/or any other tangible storage medium or media.

A computer of the invention will generally include one or more I/O device such as, for example, one or more of a video display unit (e.g., a liquid crystal display (LCD) or a cathode ray tube (CRT)), an alphanumeric input device (e.g., a keyboard), a cursor control device (e.g., a mouse), a disk drive unit, a signal generation device (e.g., a speaker), a touchscreen, an accelerometer, a microphone, a cellular radio frequency antenna, and a network interface device, which can be, for example, a network interface card (NIC), Wi-Fi card, or cellular modem.

The measurement device 701 or components of measurement device 701 may be used to perform methods described herein. Instructions for any method step may be stored in memory and a processor may execute those instructions, including use and training of a classifier for identifying cellular and non-cellular material.

The measurement device 701 thus includes at least one computer (and optionally one or more instruments) operable to identify one more live cell(s) isolated from a sample of a patient, wherein the one or more live cells comprise at least one of a cancer cell and a cancer-related immune cell. The measurement device 701 is further operable to calculate the flow velocity of a cell and correlate the identity of the cell with an SMR measurement. The measurement device 701 is optionally further operable to perform a second assay on the one or more live cells having undergone the first assay. The measurement device 701 is further operable to analyze data from the second assay and the optimized measurement from the first assay to determine at least a stage or progression of the cancer. Using the computer 701, the measurement device is operable to provide a report comprising any suitable patient information including identity along with information related to the cancer evaluation, including, but not limited to, specific data associated with the first and second assays, a determination of a stage or progression of cancer, and personalized treatment tailored to an individual patient's cancer.

Figure 8:
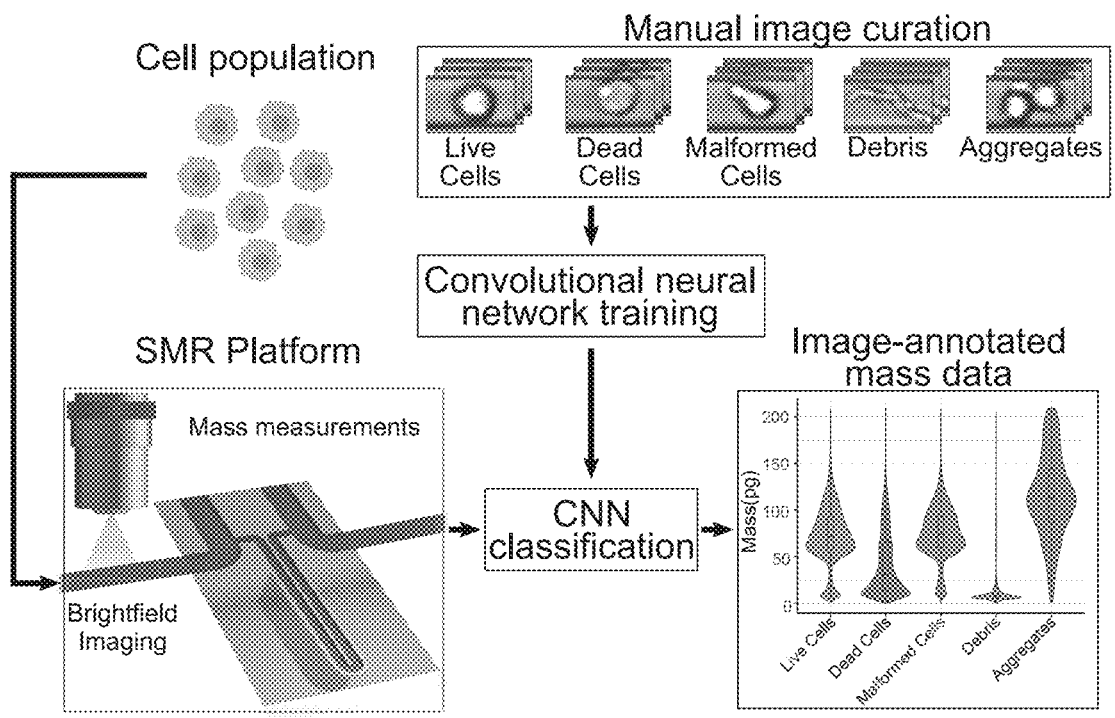
FIG. 8 shows a schematic demonstrating linked mass and imaging measurements along with exemplary data for image curated mass measurements.

FIG. 8 Shows a schematic representation of the SMR platform that allows for brightfield images to be linked with high resolution single-cell mass measurements. Using measurements of MDA-MB-361 cells, a human breast cancer cell line, images of various event types including live cells, dead cells, malformed cells, debris, and aggregates were identified. These manually curated image sets were then used to successfully train a convolution neural network (CNN) based image classification model. After applying this model to annotate additional single-cell mass measurements, there were clear signatures consistent with event types including a higher mass for particles classified as aggregates and lower mass for events classified as debris or dead cells.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

What is claimed is:

1. A measurement device for assessing properties of particles suspended in a fluid, the measurement device comprising:
  a measurement channel comprising a mass sensor to measure particle mass and an imaging sensor in a sensor region at least, wherein a particle flows through the measurement channel and sensor region, wherein the measurement device:
    obtains a plurality of images of the particle as it flows over through the sensor region and identifies the particle entering the mass sensor;
    determines a flow velocity of the particle using a positional change of the particle between images;
    uses the flow velocity of the particle to project a time at which the particle flows through the mass sensor for measurement; and
    correlates a measurement obtained using the mass sensor with the identity of the particle based on the projected time.

2. The measurement device of claim 1, wherein the measurement channel comprises at least one additional sensor.

3. The measurement device of claim 2, wherein the imaging sensor and/or additional sensor measure at least one particle property.

4. The measurement device of claim 3, further comprising means for linking multiple measurements of particles flowing within the device.

5. The measurement device of claim 4, wherein one or more signal from either the mass sensor, imaging sensor, or the additional sensor is used to link independent measurements across sensors.

6. The measurement device of claim 5, wherein independent measurements across sensors are linked by correlating a time difference between measurements of single particles across mass sensors and other sensors.

7. The measurement device of claim 6, wherein the linked measurements are used to classify single particles into groups based on orthogonal information acquired from the linked measurements.

8. The measurement device of claim 5, wherein the one or more signal is obtained in real time.

9. The measurement device of claim 4, wherein the linked single particle measurements are used to identify cells versus non-cellular material/particles or used to identify live cells versus dead cells.

10. The measurement device of claim 3, wherein the particle property is measured as a velocity and/or a trajectory.

11. The measurement device of claim 3, wherein a classifier uses data from the mass sensor, imaging sensor, and/or the additional sensor to determine one or more of the particle's mass, volume, diameter, impedance, capacitance, resistance, optical properties, density, stiffness, surface friction, deformation, cell-cycle state, viability, differentiation state, activation state, fluorescent properties.

12. The measurement device of claim 3, wherein the measurement device identifies one or more biological property of the particle using a combination of data from the additional sensor and the mass sensor.

13. The measurement device of claim 1, wherein the particle is selected from the group consisting of tissue debris, cell aggregates, bacteria, fungi, protein, protein aggregates, exosomes, biologically functionalized particles.

14. The measurement device of claim 1, wherein the sensor to measure particle mass is a suspended microchannel resonator (SMR).

15. The measurement device of claim 1, wherein the imaging sensor images multiple imaging fields.

16. The measurement device of claim 1, wherein the measurement device comprises a plurality of mass sensors and additional sensor regions, wherein each sensor region is associated with a different mass sensor, and the imaging sensor images particles flowing in each sensor region using a different field of view for each sensor region.

17. The measurement device of claim 1, wherein the mass sensor is suspended within the measurement channel and a diameter of a portion of the channel in which the mass sensor is suspended is narrower than a diameter of a portion of the channel in which the sensor region is located.

18. The measurement device of claim 1, wherein the measurement device determines whether the particle stops flowing through the measurement channel due to a blockage.

19. A measurement device for assessing properties of particles suspended in a fluid, the measurement device comprising:
  a measurement channel comprising a sensor to measure particle mass through which a particle flows and at least one additional sensor that detects the orientation of a particle in the measurement channel using the additional sensor.

20. The measurement device of claim 19, wherein the measurement device adjusts a measurement of the particle obtained using the mass sensor due to the detected orientation of the particle.

21. The measurement device of claim 19, wherein the sensor to measure particle mass is a suspended microchannel resonator (SMR).

22. The measurement device of claim 19, wherein the additional sensor is an imaging sensor.

23. A measurement device for assessing properties of particles suspended in a fluid, the measurement device comprising:
  a measurement channel comprising a sensor to measure particle mass and at least one additional sensor to measure an additional particle property,
  wherein the additional sensor detects the particle entering the mass sensor with one or more other particles and the measurement device uses data from the additional sensor to isolate a measurement for the particle from a multi-peak measurement obtained by the mass sensor due to the particle and the one or more other particles flowing through the mass sensor.

24. The measurement device of claim 23, wherein the sensor to measure particle mass is a suspended microchannel resonator (SMR).

25. The measurement device of claim 23, wherein the additional sensor is an imaging sensor.

* * * * *